United States Patent
Ichinose et al.

(10) Patent No.: US 8,981,035 B2
(45) Date of Patent: Mar. 17, 2015

(54) PRODUCTION METHOD OF POLY (PHENYLENE ETHER ETHER KETONE)

(75) Inventors: Keiko Ichinose, Nagoya (JP); Kohei Yamashita, Nagoya (JP); Makito Yokoe, Nagoya (JP); Koji Yamauchi, Nagoya (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 14/128,796

(22) PCT Filed: Jun. 22, 2012

(86) PCT No.: PCT/JP2012/004053
§ 371 (c)(1),
(2), (4) Date: Dec. 23, 2013

(87) PCT Pub. No.: WO2013/001763
PCT Pub. Date: Jan. 3, 2013

(65) Prior Publication Data
US 2014/0128565 A1  May 8, 2014

(30) Foreign Application Priority Data

Jun. 27, 2011 (JP) ................................. 2011-141511
Dec. 26, 2011 (JP) ................................. 2011-283417

(51) Int. Cl.
*C08G 8/02* (2006.01)
*C08G 65/02* (2006.01)
*C07D 323/00* (2006.01)
*C08G 65/40* (2006.01)

(52) U.S. Cl.
CPC .............. *C08G 65/02* (2013.01); *C07D 323/00* (2013.01); *C08G 65/40* (2013.01)
USPC ........... 528/126; 528/125; 528/128; 528/170; 528/172; 528/174; 528/211; 528/190; 528/216; 528/220; 528/226; 528/228

(58) Field of Classification Search
USPC ......... 525/126, 125, 128, 170, 172, 174, 190, 525/211, 216, 220, 226, 228
See application file for complete search history.

(56) References Cited

U.S. PATENT DOCUMENTS

| 4,320,224 A | 3/1982 | Rose et al. |
| 5,264,520 A | 11/1993 | Mullins et al. |
| 5,264,538 A | 11/1993 | Mullins et al. |
| 2012/0259086 A1 | 10/2012 | Yamashita et al. |

FOREIGN PATENT DOCUMENTS

| JP | 59-93724 A | 5/1984 |
| JP | 03-88828 A | 4/1991 |
| JP | 2004-51978 A | 2/2004 |
| JP | 2010-280781 A | 12/2010 |
| WO | WO 2011/081080 A | 7/2011 |

OTHER PUBLICATIONS

Xie et al. (Macromolecules 1997, 30, 4814-4827).*
International Search Report for International Application No. PCT/JP2012/004053 dated Sep. 11, 2012.
Chen, Mingfei and Gibson, Harry W.; "Large-Sized Macrocyclic Monomeric Precursors of Poly (Ether Ether Ketone): Synthesis and Polymerization"; Macromolecules 1996, vol. 29, pp. 5502-5504.

* cited by examiner

*Primary Examiner* — Shane Fang
(74) *Attorney, Agent, or Firm* — RatnerPrestia

(57) ABSTRACT

There is provided a production method of poly(phenylene ether ether ketone). The production method makes a cyclic poly(phenylene ether ether ketone) composition subjected to thermal ring-opening polymerization in the presence of a metal alkoxide and/or a metal phenoxide. The cyclic poly (phenylene ether ether ketone) composition includes 60% by weight or more of cyclic poly(phenylene ether ether ketone) and has a melting point of 270° C. or lower.

6 Claims, No Drawings

PRODUCTION METHOD OF POLY(PHENYLENE ETHER ETHER KETONE)

CROSS REFERENCE TO RELATED APPLICATIONS

This is the U.S. National Phase application of PCT International Application No. PCT/JP2012/004053, filed Jun. 22, 2012, and claims priority to Japanese Patent Application No. 2011-141511, filed Jun. 27, 2011, and Japanese Patent Application No. 2011-283417, filed Dec. 26, 2011, the disclosures of each of which applications being incorporated herein by reference in their entireties for all purposes.

FIELD OF THE INVENTION

The present invention relates to a production method of poly(phenylene ether ether ketone). More specifically the invention relates to an economical and simple method of efficiently producing poly(phenylene ether ether ketone) in a short time, which is characterized by thermal ring-opening polymerization of cyclic poly(phenylene ether ether ketone) in the presence of a polymerization initiator.

BACKGROUND OF THE INVENTION

Poly(phenylene ether ether ketone) is one of high-performance super engineering plastics and has excellent heat resistance, excellent chemical resistance and excellent flame retardancy and additionally excellent mechanical properties, such as wear resistance and friction resistance. Because of these excellent properties of poly(phenylene ether ether ketone), the demand for poly(phenylene ether ether ketone) has been expanded, as an alternative of the existing super engineering plastics or as an alternative of the existing metals, extensively in the field of automobile applications, electric and electronic applications and industrial applications.

A generally known industrial production method of this poly(phenylene ether ether ketone) is a method of polymerizing 4,4'-difluorobenzophenone and hydroquinone in diphenyl sulfone by the nucleophilic substitution reaction in the presence of a base (see, for example, Patent Document 1). This production method, however, requires an extremely high temperature of not lower than 300° C. for the reaction in its polymerization process and accordingly has a large energy cost for production. Additionally, this production method needs the use of an expensive solvent having a high boiling point, such as diphenyl sulfone. Moreover, its polymer recovery process requires a multi-stage process and a large amount of an organic solvent (for example, acetone or methanol) to wash the resulting poly(phenylene ether ether ketone) repeatedly, for example, about 10 times with the organic solvent for removal of diphenyl sulfone and subsequently wash the poly(phenylene ether ether ketone) with water for further purification. The conventional production technique of poly(phenylene ether ether ketone) accordingly has problems of extremely high production cost and high environment load.

Cyclic poly(phenylene ether ether ketone) having a poly(phenylene ether ether ketone) skeleton has recently drawn attention as the raw material used for synthesis of a high-molecular weight linear polymer by ring-opening polymerization.

The cyclic poly(phenylene ether ether ketone)s reported previously are, however, only those having the melting point of greater than 270° C.: for example, cyclic poly(phenylene ether ether ketone) having a repeating number m equal to 3 and/or 6 in General Formula (I) given below and having a melting point of 275° C. and cyclic poly(phenylene ether ether ketone) having a repeating number m equal to 4 and having a melting point of 333° C. (Non-Patent Document 1).

[Chem. 1]

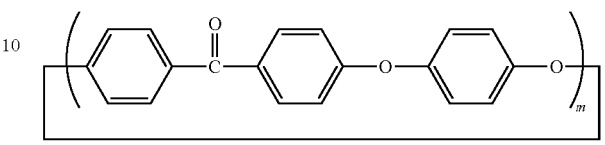

(I)

The synthesis of poly(phenylene ether ether ketone) by ring-opening polymerization of such cyclic poly(phenylene ether ether ketone) has also been reported. This synthesis is, however, performed in only a temperature range of not lower than 340° C., in other words, in a temperature range of not lower than the melting point of the conventionally known cyclic poly(phenylene ether ether ketone). There has been no description with respect to ring-opening polymerization at the temperature of not higher than the melting point of poly(phenylene ether ether ketone). This may be attributed to that the cyclic poly(phenylene ether ether ketone) used has a high melting point. This method is, however, not advantageous in energy cost, compared with the conventional production method of poly(phenylene ether ether ketone) that does not use the cyclic poly(phenylene ether ether ketone). In the process of ring-opening polymerization of the cyclic poly(phenylene ether ether ketone), the polymerization temperature may become even higher according to the composition of the raw materials used and the type and the amount of an additive added to the raw materials.

PATENT DOCUMENTS

Patent Document 1: JP S59-93724

NON-PATENT DOCUMENTS

Non-Patent Document 1: Macromolecules, volume 29, page 5502 (1996)

SUMMARY OF THE INVENTION

The present invention relates to the problems of the production method of poly(phenylene ether ether ketone) described in the above prior art, i.e., the production method of poly(phenylene ether ether ketone) without complicated production steps. More specifically, the invention makes it possible to provide an economical and simple method of efficiently producing poly(phenylene ether ether ketone) in a short time by thermal ring-opening polymerization of cyclic poly(phenylene ether ether ketone) in the presence of a polymerization initiator.

The present invention is accordingly made to solve at least part of the problems described above and may be implemented by the following embodiments.

1. There is provided a production method of poly(phenylene ether ether ketone), the production method making a cyclic poly(phenylene ether ether ketone) composition subjected to thermal ring-opening polymerization in the presence of a metal alkoxide and/or a metal phenoxide, wherein the cyclic poly(phenylene ether ether ketone) composition includes 60% by weight or more of cyclic poly(phenylene ether ether ketone) expressed by General Formula (I), the cyclic poly(phenylene ether ether ketone) is a cyclic poly (phenylene ether ether ketone) mixture having different integers m, and the composition has a melting point of 270° C. or lower:

[Chem. 2]

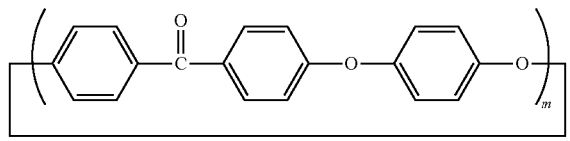

(wherein m in Formula (I) represents an integer of 2 to 40).

2. There is provided the production method of poly(phenylene ether ether ketone) described in 1 above, wherein the thermal ring-opening polymerization is performed at a temperature of 335° C. or lower.

3. There is provided the production method of poly(phenylene ether ether ketone) described in either one of 1 and 2 above, the production method adding the metal alkoxide and/or the metal phenoxide to the cyclic poly(phenylene ether ether ketone) composition, such that an addition amount of the metal alkoxide and/or the metal phenoxide is 0.001 to 50 mol % relative to 1 mol of a repeating unit expressed by a formula —(O-Ph-O-Ph-CO-Ph)-, which is a primary structural unit of the cyclic poly(phenylene ether ether ketone).

In the production method of poly(phenylene ether ether ketone) described in either one of 1 and 2 above, however, the addition amount of the metal alkoxide and/or the metal phenoxide may be less than 0.001 mol % or may be greater than 50 mol %, relative to 1 mol of the repeating unit expressed by the formula —(O-Ph-O-Ph-CO-Ph)-, which is the primary structural unit of the cyclic poly(phenylene ether ether ketone).

4. There is provided the production method of poly(phenylene ether ether ketone) described in any one of 1 to 3 above, wherein the cyclic poly(phenylene ether ether ketone) composition has a melting point of 250° C. or lower.

5. There is provided the production method of poly(phenylene ether ether ketone) described in any one of 1 to 4 above, wherein the cyclic poly(phenylene ether ether ketone) composition has a melting point of 230° C. or lower.

6. There is provided the production method of poly(phenylene ether ether ketone) described in any one of 1 to 5 above, wherein the thermal ring-opening polymerization is performed in the presence of the metal phenoxide.

7. There is provided the production method of poly(phenylene ether ether ketone) described in 6 above, wherein the metal phenoxide is at least one selected among General Formulae below:

[Chem. 3]

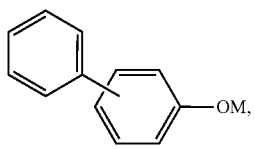

-continued

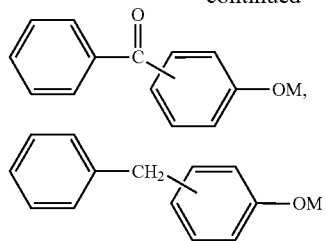

(wherein M represents at least one species selected among Li, Na, K and Cs).

8. There is provided the production method of poly(phenylene ether ether ketone) described in any one of 1 to 7 above, the production method adding an additive which has an electron-withdrawing leaving group X and is expressed by a formula $R^2$—X to the cyclic poly(phenylene ether ether ketone) composition, such that an addition amount of the additive is 0.001 to 50 mol % relative to 1 mol of a repeating unit expressed by a formula —(O-Ph-O-Ph-CO-Ph)-, which is a primary structural unit of the cyclic poly(phenylene ether ether ketone), (wherein $R^2$ represents an aliphatic group containing 1 to 20 carbon atoms or an aromatic group containing 6 to 30 carbon atoms, wherein an aromatic ring optionally includes an alkyl group, a phenyl group or another heteroatom-containing substituent group).

In the production method of poly(phenylene ether ether ketone) described in any one of 1 to 7 above, however, the addition amount of the above additive may be less than 0.001 mol % or may be greater than 50 mol %, relative to 1 mol of the repeating unit expressed by the formula —(O-Ph-O-Ph-CO-Ph)-, which is the primary structural unit of the cyclic poly(phenylene ether ether ketone).

9. There is provided poly(phenylene ether ether ketone), having an intrinsic viscosity of 0.60 to 1.80 dL/g and having a structural unit selected between an alkoxy structural unit and a phenoxy structural unit in at least one terminal structure.

10. There is provided the poly(phenylene ether ether ketone) described in 9 above, having an —$OR^2$— structure derived from an additive which has an electron-withdrawing leaving group X and is expressed by a formula $R^2$—X, in at least one terminal structure, (wherein $R^2$ represents an aliphatic group containing 1 to 20 carbon atoms or an aromatic group containing 6 to 30 carbon atoms, wherein an aromatic ring optionally includes an alkyl group, a phenyl group or another heteroatom-containing substituent group).

11. There is provided the poly(phenylene ether ether ketone) according to either one of 9 and 10 above, having a structural unit selected between an alkoxy structural unit and a phenoxy structural unit in one terminal structure and having an —$OR^2$— structure derived from an additive which has an electron-withdrawing leaving group X and is expressed by a formula $R^2$—X, in another terminal structure, (wherein $R^2$ represents an aliphatic group containing 1 to 20 carbon atoms or an aromatic group containing 6 to 30 carbon atoms, wherein an aromatic ring optionally includes an alkyl group, a phenyl group or another heteroatom-containing substituent group).

The present invention provides an economical and simple method of efficiently producing poly(phenylene ether ether ketone) in a short time. This solves the problems of the prior art, the complicated production steps, the use of an expensive organic solvent and the requirement for the polymerization reaction under high temperature in the production method of poly(phenylene ether ether ketone).

DETAILED DESCRIPTION OF THE INVENTION

The following describes embodiments of the invention in detail.

(1) Cyclic Poly(Phenylene Ether Ether Ketone)

The cyclic poly(phenylene ether ether ketone) according to an embodiment of the invention is a cyclic compound that has para-phenylene ketone and para-phenylene ether as repeating structural units and is expressed by General Formula (I) given below:

[Chem. 4]

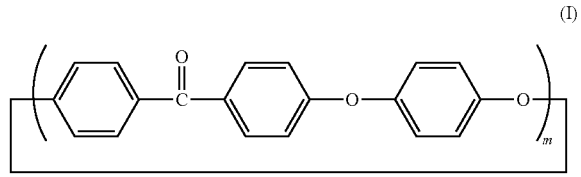

(I)

The number of repetitions m in the above Formula (I) is an integer. This number of repetitions m is preferably not less than 2 but may be greater than 2. The number of repetitions m is also preferably not greater than 40 but may be greater than 40. The number of repetitions m is more preferably not greater than 20, is furthermore preferably not greater than 15 and is especially preferably not greater than 10. The larger number of repetitions m causes the higher melting point of the cyclic poly(phenylene ether ether ketone). In terms of enabling the cyclic poly(phenylene ether ether ketone) to be fused and melted, it is accordingly preferable to set the number of repetitions m in the above range.

The cyclic poly(phenylene ether ether ketone) expressed by Formula (I) is preferably a mixture consisting of compounds having different numbers of repetitions m (hereinafter referred to as cyclic poly(phenylene ether ether ketone) mixture), is more preferably a mixture consisting of compounds having at least three or more different numbers of repetitions m, is furthermore preferably a mixture consisting of compounds having four or more different numbers of repetitions m and is especially preferably a mixture consisting of compounds having five or more different numbers of repetitions m. Additionally, it is specifically preferable that the cyclic compounds included in this cyclic poly(phenylene ether ether ketone) mixture have consecutive numbers of repetitions m. Compared with a single compound having a single number of repetitions m, a cyclic poly(phenylene ether ether ketone) mixture consisting of compounds having different numbers of repetitions m has a lower melting point. Moreover, compared with a cyclic poly(phenylene ether ether ketone) mixture consisting of compounds having two different numbers of repetitions m, a cyclic poly(phenylene ether ether ketone) mixture consisting of compounds having three or more different numbers of repetitions m has an even lower melting point. Furthermore, compared with a cyclic poly(phenylene ether ether ketone) mixture consisting of compounds having non-consecutive numbers of repetitions m, a cyclic poly(phenylene ether ether ketone) mixture consisting of compounds having consecutive numbers of repetitions m has an even lower melting point. The cyclic poly(phenylene ether ether ketone) having each number of repetitions m herein is analyzable by component separation by high-performance liquid chromatography. Additionally, the composition of the cyclic poly(phenylene ether ether ketone), i.e., the weight fraction of each of the cyclic poly(phenylene ether ether ketone)s having the respective numbers of repetitions m included in the cyclic poly(phenylene ether ether ketone) mixture is calculable from the peak area ratio of each cyclic poly(phenylene ether ether ketone) by high-performance liquid chromatography.

The cyclic poly(phenylene ether ether ketone) composition according to an embodiment of the invention has a melting point of not higher than 270° C. and is characterized by a significantly lower melting point, compared with linear poly(phenylene ether ether ketone) having a substantially equivalent molecular weight. Its melting point is preferably not higher than 250° C., is more preferably not higher than 230° C. and is furthermore preferably not higher than 180° C. The lower melting point of the cyclic poly(phenylene ether ether ketone) composition enables reduction in processing temperature during processing such as molding. Furthermore, the lower melting point enables a lower process temperature to be set in the process of producing a high polymer by using the cyclic poly(phenylene ether ether ketone) composition as a poly(phenylene ether ether ketone) prepolymer and thereby advantageously enables reduction in energy required for processing. The melting point of the cyclic poly(phenylene ether ether ketone) composition that is greater than 270° C., on the other hand, requires the high process temperature for production of a high polymer and additionally requires long-time heating. Compared with the conventional production method of poly(phenylene ether ether ketone), such a high melting point is thus unlikely to be advantageous in energy cost and is thus undesired. The melting point of the cyclic poly(phenylene ether ether ketone) composition herein is determinable by measurement of an endothermic peak temperature using a differential scanning calorimeter.

The cyclic poly(phenylene ether ether ketone) composition according to the embodiment of the invention is a composition including 60% by weight or more of the cyclic poly(phenylene ether ether ketone). The cyclic poly(phenylene ether ether ketone) composition may include more than 60% by weight of cyclic poly(phenylene ether ether ketone) and is more preferably a composition including 65% by weight or more of the cyclic poly(phenylene ether ether ketone), further more preferably a composition including 70% by weight or more of the cyclic poly(phenylene ether ether ketone) and is especially preferably a composition including 75% by weight or more of the cyclic poly(phenylene ether ether ketone). The primary impurity component of the cyclic poly(phenylene ether ether ketone) composition, i.e., the component other than the cyclic poly(phenylene ether ether ketone) is linear poly(phenylene ether ether ketone). This linear poly(phenylene ether ether ketone) has a high melting point, so that the higher weight fraction of the linear poly(phenylene ether ether ketone) results in the higher melting point of the cyclic poly(phenylene ether ether ketone) composition. The cyclic poly(phenylene ether ether ketone) composition having a low melting point is thus obtainable by setting the weight fraction of the cyclic poly(phenylene ether ether ketone) in the cyclic poly(phenylene ether ether ketone) composition to the above range. Additionally, in terms of obtaining the poly(phenylene ether ether ketone) having a sufficiently high degree of polymerization in the process of polymerization using the cyclic poly(phenylene ether ether ketone) in the cyclic poly(phenylene ether ether ketone) composition as a poly(phenylene ether ether ketone) prepolymer, it is preferable that the cyclic poly(phenylene ether ether ketone) in the cyclic poly(phenylene ether ether ketone) composition has the weight fraction in the above range. The weight fraction of the cyclic poly(phenylene ether ether ketone) in the cyclic poly(phenylene ether ether ketone) composition that is less than 60% by weight, on the other hand, interferes with high polymerization and is thus undesired.

The reduced viscosity (η) of the cyclic poly(phenylene ether ether ketone) composition according to the embodiment of the invention having the characteristics described above is, for example, preferably not higher than 0.1 dL/g, is more preferably not higher than 0.09 dL/g and is furthermore preferably not higher than 0.08 dL/g. Unless otherwise specified, the reduced viscosity according to the embodiment of the invention indicates a value measured by using an Ostwald viscosimeter at 25° C. immediately after completion of dissolution in a concentrated sulfuric acid solution having a concentration of 0.1 g/dL (weight of cyclic poly(phenylene ether ether ketone) composition/volume of 98% by weight of concentrated sulfuric acid). The calculation of the reduced viscosity follows an equation given below:

$$\eta = \{(t/t0)-1\}/C$$

(wherein t represents the number of seconds when the sample solution passes through, t0 represents the number of seconds when the solvent (98% by weight of concentrated sulfuric acid) passes through, and C represents the concentration of the solution).

The production method of the cyclic poly(phenylene ether ether ketone) according to an embodiment of the invention may be any method that can produce the cyclic poly(phenylene ether ether ketone) having the characteristics described above. An especially preferable method is a production method by reaction under heating of a mixture including at least a dihalogenated aromatic ketone compound, a base, a dihydroxy aromatic compound and an organic polar solvent.

Concrete examples of the dihalogenated aromatic ketone compound herein include 4,4'-difluorobenzophenone, 4,4'-dichlorobenzophenone, 4,4'-dibromobenzophenone, 4,4'-diiodobenzophenone, 4-fluoro-4'-chlorobenzophenone, 4-fluoro-4'-bromobenzophenone, 4-fluoro-4'-iodobenzophenone, 4-chloro-4'-bromobenzophenone, 4-chloro-4'-iodobenzophenone and 4-bromo-4'-idodobenzophenone. Among them, 4,4'-difluorobenzophenone and 4,4'-dichlorobenzophenone are preferable, and 4,4'-difluorobenzophenone is the more preferable example.

Available examples of the base include: carbonates of alkali metals such as lithium carbonate, sodium carbonate, potassium carbonate, rubidium carbonate and cesium carbonate; carbonates of alkaline earth metals such as calcium carbonate, strontium carbonate and barium carbonate; bicarbonates of alkali metals such as lithium hydrogen carbonate, sodium hydrogen carbonate, potassium hydrogen carbonate, rubidium hydrogen carbonate and cesium hydrogen carbonate; bicarbonates of alkaline earth metals such as calcium hydrogen carbonate, strontium hydrogen carbonate and barium hydrogen carbonate; hydroxides of alkali metals such as lithium hydroxide, sodium hydroxide, potassium hydroxide, rubidium hydroxide and cesium hydroxide; and hydroxides of alkaline earth metals such as calcium hydroxide, strontium hydroxide and barium hydroxide. Among them, in terms of the economic efficiency and the reactivity, preferable are carbonates such as sodium carbonate and potassium carbonate and bicarbonates such as sodium hydrogen carbonate and potassium hydrogen carbonate, and more preferable are sodium carbonate and potassium carbonate. Any of these bases may be used alone, or two or more of these bases may be used as a mixture. The alkali is preferably used in the form of an anhydride but may also be used as a hydrate or an aqueous mixture. The aqueous mixture herein indicates an aqueous solution, a mixture of an aqueous solution and a solid component or a mixture of water and a slid component.

Preferable concrete examples of the dihydroxy aromatic compound used according to the embodiment of the invention are hydroquinone and 4,4'-dihydroxybenzophenone. Especially preferable is hydroquinone. Any of these dihydroxy aromatic compounds may be used alone, or two or more of these dihydroxy aromatic compounds may be used as a mixture.

The used amount of the dihydroxy aromatic compound is preferably not less than 0.80 mol relative to 1.0 mol of the dihalogenated aromatic ketone compound, is more preferably not less than 0.90 mol, is furthermore preferably not less than 0.95 mol and is especially preferably not less than 0.98 mol. The used amount of the dihydroxy aromatic compound is also preferably not greater than 1.20 mol relative to 1.0 mol of the dihalogenated aromatic ketone compound, is more preferably not greater than 1.10 mol, is furthermore preferably not greater than 1.05 mol and is especially preferably not greater than 1.03 mol. Controlling the used amount of the dihydroxy aromatic compound to the above preferable range can interfere with a decomposition reaction of the produced cyclic poly(phenylene ether ether ketone) and can also interfere with production of the linear poly(phenylene ether ether ketone), which is difficult to be separated from the cyclic poly(phenylene ether ether ketone).

The organic polar solvent used for production of the cyclic poly(phenylene ether ether ketone) according to the invention is not specifically limited but may be any organic polar solvent that does not substantially interfere with the reaction and does not substantially cause an undesired side reaction, such as decomposition of the produced cyclic poly(phenylene ether ether ketone). Concrete examples of such an organic polar solvent include: nitrogen-containing polar solvents such as N-methyl-2-pyrrolidone, N-methylcaprolactam, N,N-dimethylformamide, N—N-dimethylacetamide, 1,3-dimethyl-2-imidazolidinone, hyexamethylphosphoramide and tetramethylurea; sulfoxide and sulfone solvents such as dimethyl sulfoxide, dimethyl sulfone, diphenyl sulfone and sulfolane; nitrile solvents such as benzonitrile; diaryl ethers such as diphenyl ether; ketones such as benzophenone and acetophenone; and mixtures thereof. Any of these organic polar solvents has the high stability of the reaction and is thus preferably used. Among them, preferable are N-methyl-2-pyrrolidone and dimethyl sulfoxide, and especially preferable is N-methyl-2-pyrrolidone. These organic polar solvents have excellent stability in a high temperature range and are also preferable in terms of the availability.

The amount of the organic polar solvent used for synthesis of the cyclic poly(phenylene ether ether ketone) by the above production method is preferably not less than 1.15 liters relative to 1.0 mol of the benzene ring component in the mixture including at least the dihalogenated aromatic ketone compound, the base, the dihydroxy aromatic compound and the organic polar solvent, is more preferably not less than 1.30 liters, is furthermore preferably not less than 1.50 liters and is especially preferably not less than 2.00 liters. The upper limit of the used amount of the organic polar solvent is not specifically restricted, but is preferably not greater than 100 liters relative to 1.0 mol of the benzene ring component in the above mixture, is more preferably not greater than 50 liters, is furthermore preferably not greater than 20 liters and is especially preferably not greater than 10 liters. Increasing the used amount of the organic polar solvent improves the selectivity in production of the cyclic poly(phenylene ether ether ketone). The excessively increased amount of the organic polar solvent, however, reduces the amount of production of the cyclic poly(phenylene ether ether ketone) per unit volume of a reaction vessel and additionally increases the time required for the reaction. Accordingly, controlling the used amount of the organic polar solvent to the above range is preferable, in terms of satisfying both the production selectivity and the productivity of the cyclic poly(phenylene ether ether ketone). The amount of the organic polar solvent herein is indicated by a volume of the solvent at ordinary temperatures and ordinary pressures. The used amount of the organic polar solvent in the reaction mixture is a value obtained by subtracting the amount of the organic polar solvent expelled out of the reaction system during, for example, dehydration operation from the amount of the organic polar solvent introduced into the reaction system. The benzene ring component in the mixture herein means a benzene ring component included in the raw materials which can become structural components of the cyclic poly(phenylene ether ether ketone) by the reaction. The "molar number" of the benzene ring component in these raw materials indicates the "number of benzene rings constituting the compound". For example, 1 mol of 4,4'-difluorobenzophenone corresponds to 2 mol of the benzene ring component, and 1 mol of hydroquinone corresponds to 1 mol of the benzene ring component. Accordingly, a mixture including 1 mol of 4,4'-difluorobenzophenone and 1 mol of hydroquinone, is a mixture including 3 mol of the benzene ring component. The component that cannot become a structural component of the cyclic poly(phenylene ether ether ketone) by the reaction, for example, toluene is regarded to be 0 mol of the benzene ring component.

The used amount of the base in the production method of the cyclic poly(phenylene ether ether ketone) by the reaction under heating of the mixture including at least the dihalogenated aromatic ketone compound, the base, the dihydroxy aromatic compound and the organic polar solvent may be any ratio greater than the stoichiometric ratio relative to the dihydroxy aromatic compound. For example, when the used amount of a divalent base such as sodium carbonate or potassium carbonate is equal to A mol and the used amount of a monovalent base such as sodium hydrogen carbonate or potassium hydrogen carbonate is equal to B mol, it is desirable that (A+2B) as the specific used amount of the base is not less than 1.00 mol relative to 1.0 mol of the dihydroxy aromatic compound. This value of (A+2B) is also preferably not greater than 1.10 mol, is more preferably not greater than 1.05 mol and is furthermore preferably not greater than 1.03 mol. When a separately prepared metal salt of a dihydroxy aromatic compound is used for production of the cyclic poly(phenylene ether ether ketone), an excess amount of the base may be supplied by addition of the base. The supplied excess amount of the base expressed by (A+2B) is preferably not less than 0.00 mol relative to 1.0 mol of the dihydroxy aromatic compound used for production of the cyclic poly(phenylene ether ether ketone) and is preferably not greater than 0.10 mol, is more preferably not greater than 0.05 mol and is furthermore preferably not greater than 0.03 mol. Controlling the used amount of the base for production of the cyclic poly(phenylene ether ether ketone) enables sufficient production of the metal salt of the dihydroxy aromatic compound and additionally interferes with the progress of an undesired reaction induced by an excess base, such as decomposition reaction of the produced cyclic poly(phenylene ether ether ketone).

The reaction temperature of the reaction under heating of the mixture including at least the dihalogenated aromatic ketone compound, the base, the dihydroxy aromatic compound and the organic polar solvent differs according to the types and the amounts of the raw materials included in the mixture and is thus not unequivocally specifiable, but is generally not lower than 120° C., is preferably not lower than 130° C. and is more preferably not lower than 140° C. This reaction temperature is also not higher than 350° C., is preferably not higher than 320° C. and is more preferably not higher than 300° C. This desired temperature range ensures the higher reaction rate. The reaction herein may be any of a single-stage reaction that maintains a constant temperature, a multi-stage reaction that raises the temperature stepwise and a reaction that changes the temperature continuously.

The reaction time depends on the types and the amounts of the raw materials used or the reaction temperature and is thus not unequivocally specifiable but is preferably not shorter than 0.1 hours, is more preferably not shorter than 0.5 hours and is furthermore preferably not shorter than 1 hour. The reaction time of not shorter than this desired time enables sufficient reduction of unreacted raw material components. The upper limit of the reaction time is, on the other hand, not specifically restricted. The reaction sufficiently proceeds in 40 hours, and the reaction time is preferably not longer than 10 hours and is more preferably not longer than 6 hours.

In the reaction under heating of the mixture including at least the dihalogenated aromatic ketone compound, the base, the dihydroxy aromatic compound and the organic polar solvent, a component which does not significantly interfere with the reaction or a component which has the effect of accelerating the reaction may be added to this mixture, in addition to the above essential components. The conditions of the reaction are not specifically limited, but it is preferable that the reaction proceeds under the stirring condition. Additionally, any of known various polymerization systems and reaction systems, such as batch system or continuous system, may be employed for the production method of the cyclic poly(phenylene ether ether ketone) according to the invention. The atmosphere for the production is desirably a non-oxidizing atmosphere. The production is preferably performed under an inert atmosphere such as nitrogen, helium or argon. In terms of the economic efficiency and the easiness of handling, the production is more preferably performed under nitrogen atmosphere.

The presence of a large amount of water in the reaction system causes adverse effects on the above reaction, for example, reduction of the reaction rate and production of a byproduct, which is difficult to be separated from the cyclic poly(phenylene ether ether ketone). It is accordingly preferable to expel the water in the case of using a hydrate or an aqueous mixture as the base or the water produced as the byproduct of the reaction, out of the reaction system. The water content present in the system during the reaction is preferably not higher than 2.0% by weight, is more preferably not higher than 1.0% by weight, is furthermore preferably not higher than 0.5% by weight and is especially preferably not higher than 0.1% by weight. A dehydration operation may be performed optionally to control the water content to this desired range. The water content present in the system herein is expressed by the weight fraction relative to the total weight of the reaction mixture and is measurable by the Karl Fischer method. The timing of the dehydration operation is not specifically limited but is preferable (A) after mixing the essential components or (B) after mixing the essential components other than the dihalogenated aromatic ketone compound. When the dehydration operation is performed at the timing (B), the cyclic poly(phenylene ether ether ketone) is produced by adding the dihalogenated aromatic ketone compound or the dihalogenated aromatic ketone compound and the organic polar solvent after the dehydration operation. The method of removing water may be any method that can expel water out of the reaction system, for example, dehydration by high temperature heating or the method by azeotropic distillation using an azeotropic solvent. In terms of the dehydration efficiency, the method by azeotropic distillation is especially preferable. The azeotropic solvent used for azeotropic distillation may be any organic compound which can form an azeotropic mixture with water, wherein the boiling point of the azeotropic mixture is lower than the boiling point of the organic polar solvent used for the reaction. Concrete examples of the azeotropic solvent include: hydrocarbon solvents such as hexane, cyclohexane, heptane, benzene, toluene and xylene; and inactive chlorinated aromatic compounds such as chlorobenzene and dichlorobenzene. Among them, toluene and xylene are preferably used as the azeotropic solvent. The amount of the azeotropic solvent required for formation of the azeotropic mixture with water differs according to the amount of water present in the system and the type of the solvent and is thus not unequivocally specifiable. It is, however, preferable to use an excess amount of the azeotropic solvent that is greater than the required amount for removing the water present in the reaction system as the azeotropic mixture. More specifically, the amount of the azeotropic solvent is preferably not less than 0.2 liters relative to 1.0 mol of the dihalogenated aromatic ketone compound in the mixture, is more preferably not less than 0.5 liters and is furthermore preferably not less than 1.0 liter. The upper limit of the amount of the azeotropic solvent is, on the other hand, not specifically restricted but is preferably not greater than 20.0 liters relative to 1.0 mol of the dihalogenated aromatic ketone compound in the mixture, is more preferably not greater than 10.0 liters and is furthermore preferably not greater than 5.0 liters. The excessively large amount of the azeotropic solvent, however, lowers the polarity of the mixture and thereby reduces the efficiency of the reaction of the base with the dihalogenated aromatic ketone compound or the efficiency of the reaction of the base with the dihydroxy aromatic compound. The amount of the azeotropic solvent herein is expressed by the volume of the solvent at ordinary temperatures and ordinary pressures. When azeotropic distillation of water is performed by using the principle of a Dean-Stark apparatus, the amount of the azeotropic solvent in the reaction system can be maintained constant, so that the used amount of the azeotropic solvent can be further reduced. The temperature for expelling water out of the reaction system is not unequivocally specifiable, since the boiling point of the azeotropic mixture with water differs according to the type of the azeotropic solvent. The temperature is preferably not lower than the boiling point of the azeotropic mixture with water but not higher than the boiling point of the organic polar solvent used for the reaction. More specifically, the temperature for expelling water out of the reaction system may be in the range of 60 to 170° C., preferably in the range of 80 to 170° C., more preferably in the range of 100 to 170° C. and furthermore preferably in the range of 120 to 170° C. The method of removing water may be any of a method that maintains a constant temperature in the desired temperature range, a method that raises the temperature stepwise and a temperature that changes the temperature continuously. Additionally, it is also preferable to perform the above azeotropic distillation under reduced pressure. The azeotropic distillation under reduced pressure enables the more efficient removal of water.

It is preferable to expel the above azeotropic solvent out of the system after the azeotropic distillation. The timing of expelling the azeotropic solvent out of the system is preferably after completion of the azeotropic distillation of water. Additionally, when the dehydration operation is performed at the above timing (B), it is preferable to remove the azeotropic solvent at the stage prior to addition of the dihalogenated aromatic ketone compound or at the stage prior to addition of the dihalogenated aromatic ketone compound and the organic polar solvent. A large amount of the azeotropic solvent remaining in the system lowers the polarity of the reaction system and reduces the reaction rate of production of the cyclic poly(phenylene ether ether ketone). The removal operation of the azeotropic solvent is thus required. The amount of the azeotropic solvent present in the system during the production reaction of the cyclic poly(phenylene ether ether ketone) is preferably not greater than 20% relative to the amount of the organic polar solvent used for the production reaction of the cyclic poly(phenylene ether ether ketone), is more preferably not greater than 10%, is furthermore preferably not greater than 8% and is especially preferably not greater than 6%. The azeotropic solvent should be removed, such that the amount of the azeotropic solvent is not greater than this desired range. The method of removing the azeotropic solvent is preferably a method by distillation and may use an inert gas, such as nitrogen, helium or argon, as the carrier gas. The preferable method performs distillation under reduced pressure. This enables the more efficient removal of the azeotropic solvent. The temperature for removing the azeotropic solvent may be any temperature that can expel the azeotropic solvent out of the reaction system and is specifically in the range of 60 to 170° C., is preferably in the range of 100 to 170° C., is more preferably in the range of 120 to 170° C. and is furthermore preferably in the range of 140 to 170° C. The method of removing the azeotropic solvent may be any of a method that maintains a constant temperature in the desired temperature range, a method that raises the temperature stepwise and a temperature that changes the temperature continuously.

The cyclic poly(phenylene ether ether ketone) composition according to the embodiment of the invention is obtainable by an operation of separation and recovery of the cyclic poly(phenylene ether ether ketone) from a reaction product obtained by the production method of the cyclic poly(phenylene ether ether ketone) described above. The reaction product obtained by the above production method includes at least the cyclic poly(phenylene ether ether ketone), the linear poly(phenylene ether ether ketone) and the organic polar solvent and may additionally include unreacted raw materials, a byproduct salt, water and the azeotropic solvent as other components The method of recovering the cyclic poly(phenylene ether ether ketone) from this reaction product is not specifically limited. For example, one available method may add an organic polar solvent having low solubility for the poly(phenylene ether ether ketone) component after optionally removing part or most of the organic polar solvent used for the reaction by an operation such as distillation and cause the added organic polar solvent to be exposed to a solvent having solubility for the byproduct salt, optionally under heating, so as to recover the cyclic poly(phenylene ether ether ketone) in the form of a solid mixture with the linear poly(phenylene ether ether ketone). The solvent having this characteristic is generally a solvent of relatively high polarity but is not specifiable since the desired solvent differs according to the organic polar solvent used and the type of the byproduct salt. Available examples of the solvent include: water; alcohols such as methanol, ethanol, propanol, isopropyl alcohol, butanol and hexanol; ketones such as acetone and methyl ethyl ketone; and acetate esters such as ethyl acetate and butyl acetate. In terms of the availability and the economic efficiency, preferable are water, methanol and acetone, and especially preferable is water.

Such treatment using the solvent can reduce the amount of the organic polar solvent and the amount of the byproduct salt included in the solid mixture of the cyclic poly(phenylene ether ether ketone) and the linear poly(phenylene ether ether ketone). This treatment enables both the cyclic poly(phenylene ether ether ketone) and the linear poly(phenylene ether ether ketone) to precipitate as solid components and thus enables recovery of a mixture of the cyclic poly(phenylene ether ether ketone) and the linear poly(phenylene ether ether ketone) by a known solid liquid separation method. The solid liquid separation method may be, for example, separation by filtration, centrifugal separation or decantation. The series of these treatments may be repeated a plurality of times as needed basis. This further reduces the amount of the organic polar solvent and the amount of the byproduct salt included in the solid mixture of the cyclic poly(phenylene ether ether ketone) and the linear poly(phenylene ether ether ketone).

The method of the treatment using the solvent described above may be a method of mixing the solvent with the above reaction product with optionally stirring or heating in an adequate manner. The temperature of the treatment using the solvent is not specifically limited but is preferably not lower than 20° C. and is more preferably not lower than 50° C. The temperature of the treatment using the solvent is also preferably not higher than 220° C. and is more preferably not higher than 200° C. This temperature range is preferable since this facilitates removal of, for example, the byproduct salt and enables the treatment in a relatively low pressure state. When water is used as the solvent, the water is preferably distilled water or deionized water but may be used in the form of an aqueous solution including an acidic organic compound such as formic acid, acetic acid, propionic acid, butyric acid, chloroacetic acid, dichloroacetic acid, acrylic acid, crotonic acid, benzoic acid, salicylic acid, oxalic acid, malonic acid, succinic acid, phthalic acid or fumaric acid or its alkali metal salt or alkaline earth metal salt. Also usable is an aqueous solution including an acidic inorganic compound such as sulfuric acid, phosphoric acid, hydrochloric acid, carbonic acid or silicic acid or an ammonium ion. When the solid mixture of the cyclic poly(phenylene ether ether ketone) and the linear poly (phenylene ether ether ketone) obtained after this treatment contains the solvent used for the treatment, the solvent may be optionally removed by, for example, drying.

The above recovery method causes the cyclic poly(phenylene ether ether ketone) to be recovered in the form of a mixture with the linear poly(phenylene ether ether ketone) (hereinafter referred to as recovered mixture). The cyclic poly(phenylene ether ether ketone) composition is obtainable from this recovered mixture. In order to further increase the content of the cyclic poly(phenylene ether ether ketone) in the cyclic poly(phenylene ether ether ketone) composition, the employed method of separation and recovery of the cyclic poly(phenylene ether ether ketone) from the recovered mixture may be, for example, a separation method using the difference in solubility between the cyclic poly(phenylene ether ether ketone) and the linear poly(phenylene ether ether ketone). More specifically, an available method exposes the above recovered mixture, optionally under heating, to a solvent having high solubility for the cyclic poly(phenylene ether ether ketone) but poor solubility for the linear poly (phenylene ether ether ketone), so as to obtain the cyclic poly(phenylene ether ether ketone) as a solvent-soluble component. It is generally known that the linear poly(phenylene ether ether ketone) has the characteristics of high crystallinity and extremely low solubility in the solvent. There is accordingly a significant difference in solubility in the solvent between the cyclic poly(phenylene ether ether ketone) and the linear poly(phenylene ether ether ketone). The cyclic poly (phenylene ether ether ketone) composition having a large content of the cyclic poly(phenylene ether ether ketone) can thus be obtained efficiently by the above separation method using the difference in solubility.

The solvent used herein is not specifically limited but may be any solvent that can dissolve the cyclic poly(phenylene ether ether ketone). Preferable is a solvent that dissolves the cyclic poly(phenylene ether ether ketone) but only slightly dissolves the linear poly(phenylene ether ether ketone), and more preferable is a solvent that does not dissolve the linear poly(phenylene ether ether ketone). The pressure in the reaction system in the process of exposing the above recovered mixture to the above solvent is preferably ordinary pressure or slightly pressurized and is especially preferably ordinary pressure. The reaction system under such pressure has the advantage that structural members of a reactor are inexpensive. From this point of view, it is preferable to avoid a pressurized condition that requires an expensive pressure vessel for the pressure in the reaction system. The solvent used is preferably a solvent that does not substantially induce an undesired side reaction, such as decomposition or cross-linking of the poly(phenylene ether ether ketone) component. Examples of the solvent preferably used for the operation of exposing the above recovered mixture to the solvent, for example, under the condition of reflux at normal pressure include: hydrocarbon solvents such as pentane, hexane, heptane, octane, cyclohexane, cyclopentane, benzene, toluene and xylene; halogenated solvents such as chloroform, bromoform, methylene chloride, 1,2-dichloroethane, 1,1,1-trichloroethane, chlorobenzene and 2,6-dichlorotoluene; ether solvents such as diethyl ether, tetrahydrofuran and diisopropyl ether; and polar solvents such as N,N-dimethylformamide, N,N-dimethylacetamide, dimethyl sulfoxide, trimethyl phosphate and N,N-dimethylimidazolidinone. Among them, preferable are benzene, toluene, xylene, chloroform, bromoform, methylene chloride, 1,2-dichloroethane, 1,1,1-trichloroethane, chlorobenzene, 2,6-dichlorotoluene, diethyl ether, tetrahydrofuran, diisopropyl ether, N,N-dimethylformamide, N,N-dimethylacetamide, dimethyl sulfoxide, trimethyl phosphate and N,N-dimethylimidazolidinone. More preferable are toluene, xylene, chloroform, methylene chloride and tetrahydrofuran.

The atmosphere for exposing the above recovered mixture to the solvent is not specifically limited but is preferably a non-oxidizing atmosphere. It is preferable to perform the exposure under an inert gas atmosphere such as nitrogen, helium or argon. Among them, in terms of the economic efficiency and the easiness of handling, it is especially preferable to perform the exposure under nitrogen atmosphere.

The temperature for exposing the above recovered mixture to the solvent is not specifically limited. The higher temperature generally accelerates dissolution of the cyclic poly(phenylene ether ether ketone) in the solvent. As described above, it is preferable to expose the above recovered mixture to the solvent under ordinary pressure. The upper limit temperature is thus preferably the reflux temperature (boiling point) of the used solvent under atmospheric pressure. When any of the preferable solvents described above is used, the specific temperature range is, for example, 20 to 150° C.

The time for exposing the above recovered mixture to the solvent differs according to the type of the solvent used and the temperature and is thus not unequivocally specifiable but may be, for example 1 minute to 50 hours. This ranges enables the cyclic poly(phenylene ether ether ketone) to be sufficiently dissolved in the solvent.

The method of exposing the above recovered mixture to the solvent is not specifically limited, but any of known general techniques may be employed. Available methods include: for example, a method that mixes the recovered mixture with the solvent, optionally with stirring and subsequently recovers the solution part; a method that sprays the solvent onto the above mixture on any of various filters and simultaneously dissolves the cyclic poly(phenylene ether ether ketone) in the solvent; and a method that employs the principle of the Soxhlet extraction method. The used amount of the solvent in exposure of the recovered mixture to the solvent is not specifically limited but may be in a range of 0.5 to 100 [L/kg] as the liquor ratio to the weight of recovered mixture. The liquor ratio in this range facilitates the above recovered mixture to be homogeneously mixed with the solvent and also facilitates the cyclic poly(phenylene ether ether ketone) to be sufficiently dissolved in the solvent. The larger liquor ratio is generally advantageous for dissolution of the cyclic poly (phenylene ether ether ketone) in the solvent. The excessively large liquor ratio is, however, not expected to have any further effects but may, on the contrary, cause economical disadvantage due to an increase in used amount of the solvent. In the case of repeating the exposure of the above recovered mixture to the solvent, even the small liquor ratio often achieves the sufficient effects. The Soxhlet extraction method has the similar effects in principle and thus often allows even the small liquor ratio to achieve the sufficient effects.

When the solution with the cyclic poly(phenylene ether ether ketone) dissolved therein is obtained as a solid-liquid slurry including the linear poly(phenylene ether ether ketone) after the exposure of the above recovered mixture to the solvent, it is preferable to recover the solution part by a known solid liquid separation method. The solid liquid separation method may be, for example, separation by filtration, centrifugal separation or decantation. Removing the solvent from the separated solution in this manner enables recovery of the cyclic poly(phenylene ether ether ketone). When the cyclic poly(phenylene ether ether ketone) still remains in the solid component, the exposure to the solvent and the recovery of the solution may be repeatedly performed to obtain the cyclic poly(phenylene ether ether ketone) in good yield.

The cyclic poly(phenylene ether ether ketone) can be obtained as a solid component by removing the solvent from the solution including the cyclic poly(phenylene ether ether ketone) obtained as described above. The solvent may be removed by, for example, a method of heating the solution under ordinary pressure or a method using a membrane for removal of the solvent. In terms of efficiently obtaining the cyclic poly(phenylene ether ether ketone) in good yield, preferable is a method of heating the solution at ordinary pressure or below to remove the solvent. The solution including the cyclic poly(phenylene ether ether ketone) obtained as described above may include a solid matter at some temperature. In this case, the solid matter arises from the cyclic poly(phenylene ether ether ketone), so that it is preferable to recover the solid matter with the component soluble in the solvent in the process of removal of the solvent. This increases the yield of the cyclic poly(phenylene ether ether ketone). The removal of the solvent removes at least not less than 50% by weight of the solvent, preferably not less than 70% by weight of the solvent, more preferably not less than 90% by weight of the solvent and furthermore preferably not less than 95% of the solvent. The temperature for removal of the solvent by heating depends on the type of the solvent used and is not unequivocally specifiable, but is generally selected in the range of 20 to 150° C. and is preferably selected in the range of 40 to 120° C. The pressure for removal of the solvent is preferably ordinary pressure or below. This enables removal of the solvent at low temperature. The cyclic poly (phenylene ether ether ketone) composition according to the embodiment of the invention is obtainable by the steps described above.

(2) Production Method of Poly(Phenylene Ether Ether Ketone) The following describes a production method of poly(phenylene ether ether ketone) using the cyclic poly(phenylene ether ether ketone) composition according to an embodiment of the invention.

An embodiment of the invention is characterized by production of the poly(phenylene ether ether ketone) by thermal ring-opening polymerization of the above cyclic poly(phenylene ether ether ketone) composition in the presence of a metal alkoxide and/or a metal phenoxide.

The poly(phenylene ether ether ketone) according to the embodiment of the invention herein is a linear compound that has para-phenylene ketone and para-phenylene ether as repeating structural units and is expressed by General Formula (II) given below:

[Chem. 5]

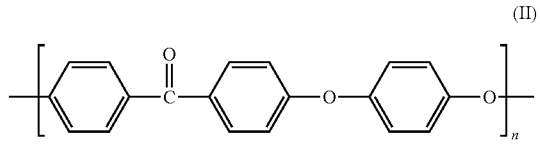

(II)

The number of repetitions n in Formula (II) is not specifically limited but is preferably not less than 10, is more preferably not less than 20 and is furthermore preferably not less than 30. The number of repetitions n is also preferably not greater than 10000, is more preferably not greater than 5000 and is furthermore preferably not greater than 1000.

The heating temperature in the process of converting the cyclic poly(phenylene ether ether ketone) in the cyclic poly (phenylene ether ether ketone) composition according to the embodiment of the invention into the poly(phenylene ether ether ketone) by thermal ring-opening polymerization is preferably not less than a temperature of fusing and melting the cyclic poly(phenylene ether ether ketone) composition. When the heating temperature is less than the melting point of the cyclic poly(phenylene ether ether ketone) composition, it takes a long time to obtain the poly(phenylene ether ether ketone) by thermal ring-opening polymerization. Otherwise the thermal ring-opening polymerization does not proceed and fails to give sufficiently highly polymerized poly(phenylene ether ether ketone). The temperature of fusing and melting the cyclic poly(phenylene ether ether ketone) composition differs according to the formulation of the cyclic poly(phenylene ether ether ketone) composition, the molecular weights of the respective components included in the cyclic poly(phenylene ether ether ketone) composition, the weight fraction of the cyclic poly(phenylene ether ether ketone) included in the cyclic poly(phenylene ether ether ketone) composition and the environment during heating and is thus not unequivocally specifiable. The melting point may, however, be obtained, for example, by analyzing the cyclic poly(phenylene ether ether ketone) composition by a differential scanning calorimeter. The lower limit of the heating temperature is, for example, not lower than 150° C., is preferably not lower than 180° C., is more preferably not lower than 200° C. and is furthermore preferably not lower than 220° C. In this temperature range, the cyclic poly(phenylene ether ether ketone) composition is fused and melted, so that the poly(phenylene ether ether ketone) is obtainable in a short time. The excessively high temperature for the thermal ring-opening polymerization, on the other hand, facilitates the occurrence of undesired side reactions, for example, cross-linking reactions between the cyclic poly(phenylene ether ether ketone)s, between the resulting poly(phenylene ether ether ketone)s and between the resulting poly(phenylene ether ether ketone) and the cyclic poly(phenylene ether ether ketone), and decomposition reactions. This may result in degrading the properties of the obtained poly(phenylene ether ether ketone). It is accordingly preferable to avoid the temperature that significantly causes such undesired side reactions. The upper limit of the heating temperature is, for example, not higher than 500° C., is preferably not higher than 400° C., is more preferably not higher than 360° C., is furthermore preferably not higher than 335° C., is especially preferably not higher than 320° C. and is more especially preferably not higher than 300° C. The heating temperature of not higher than this temperature range reduces the adverse effects on the properties of the resulting poly(phenylene ether ether ketone) caused by the undesired side reactions and additionally reduces the energy cost required for production.

The known cyclic poly(phenylene ether ether ketone) described above, i.e., the cyclic poly(phenylene ether ether ketone) having the melting point of higher than 270° C. requires a long time for the thermal ring-opening polymerization in the above preferable temperature range, due to the high melting point of the cyclic poly(phenylene ether ether ketone). Otherwise the thermal ring-opening polymerization does not proceed and fails to give sufficiently highly polymerized poly(phenylene ether ether ketone). The cyclic poly(phenylene ether ether ketone) composition according to the embodiment of the invention that is characterized by the melting point of not higher than 270° C., on the other hand, enables the thermal ring-opening polymerization to efficiently proceed in the above preferable temperature range and give sufficiently highly polymerized poly(phenylene ether ether ketone).

The time of the thermal ring-opening polymerization according to the embodiment of the invention differs according to various conditions, for example, the weight fraction and the composition ratio of the cyclic poly(phenylene ether ether ketone) in the used cyclic poly(phenylene ether ether ketone) composition, the heating temperature and the method of thermal ring-opening polymerization and is thus not unequivocally specifiable. It is, however, preferable to set the time of the thermal ring-opening polymerization, in order to interfere with the undesired side reactions, such as the cross-linking reactions described above. More specifically, the time of the thermal ring-opening polymerization is preferably not shorter than 0.5 minutes, is more preferably not shorter than 1 minute, is furthermore preferably not shorter than 3 minutes, is especially preferably not shorter than 4 minutes and is more especially preferably not shorter than 5 minutes. The time of the thermal ring-opening polymerization is also preferably not longer than 3000 minutes, is more preferably not longer than 1200 minutes, is furthermore preferably not longer than 600 minutes, is especially preferably not longer than 300 minutes and is more especially preferably not longer than 240 minutes. Setting this preferable time of the thermal ring-opening polymerization facilitates conversion of the cyclic poly(phenylene ether ether ketone) in the cyclic poly(phenylene ether ether ketone) composition into the poly(phenylene ether ether ketone) to sufficiently proceed and additionally reduces adverse effects on the properties of the produced poly(phenylene ether ether ketone) caused by the progress of the undesired side reactions, such as the cross-linking reactions.

The metal alkoxide and/or the metal phenoxide used for conversion of the cyclic poly(phenylene ether ether ketone) in the cyclic poly(phenylene ether ether ketone) composition according to the embodiment of the invention into the poly(phenylene ether ether ketone) serves as an anionic polymerization initiator of the ring-opening polymerization. Concrete examples of the metal alkoxide include alkali metal salts of aliphatic alcohols containing 1 to 20 carbon atoms, such as sodium methoxide, potassium methoxide, lithium methoxide, cesium methoxide, sodium ethoxide, potassium ethoxide, lithium ethoxide, cesium ethoxide, sodium n-butoxide, potassium n-butoxide, lithium n-butoxide, cesium n-butoxide, sodium s-butoxide, potassium s-butoxide, lithium s-butoxide, cesium s-butoxide, sodium t-butoxide, potassium t-butoxide, lithium t-butoxide, cesium t-butoxide, sodium n-propoxide, potassium n-propoxide, lithium n-propoxide, cesium n-propoxide, sodium isopropoxide, potassium isopropoxide, lithium isopropoxide, cesium isopropoxide, sodium cyclohexanolate, potassium cyclohexanolate, lithium cyclohexanolate and cesium cyclohexanolate. Concrete examples of the metal phenoxide include: alkali metal salts of phenols, such as sodium phenoxide, potassium phenoxide, lithium phenoxide, cesium phenoxide, sodium 4-phenylphenoxide, potassium 4-phenylphenoxide, lithium 4-phenylphenoxide, cesium 4-phenylphenoxide, sodium 4-phenoxyphenoxide, potassium 4-phenoxyphenoxide, lithium 4-phenoxyphenoxide, cesium 4-phenoxyphenoxide, sodium 4-benzoylphenoxide, potassium 4-benzoylphenoxide, lithium 4-benzoylphenoxide, cesium 4-benzoylphenoxide, sodium 2-benzylphenoxide, potassium 2-benzylphenoxide, lithium 2-benzylphenoxide, sodium 4-benzylphenoxide, potassium 4-benzylphenoxide and lithium 4-benzylphenoxide; alkali metal salts of bisphenols, such as sodium salt of 4,4-dihydroxybiphenyl, potassium salt of 4,4-dihydroxybiphenyl, lithium salt of 4,4-dihydroxybiphenyl, cesium salt of 4,4-dihydroxybiphenyl, sodium salt of bisphenol A, potassium salt of bisphenol A, lithium salt of bisphenol A and cesium salt of bisphenol A. The aromatic ring in the above phenoxide may include a substituent group, for example, an alkyl group, a phenyl group, a halogen atom or another heteroatom-containing functional group. The metal phenoxide is preferably used as this anionic polymerization initiator, since the metal phenoxide has high thermal stability even at the temperature of not lower than 150° C., which is suitable for the thermal ring-opening polymerization of the poly(phenylene ether ether ketone) and is easily handled. Among them, especially preferable is a metal phenoxide expressed by general formulae given below. Using this especially preferable metal phenoxide facilitates the polymerization to sufficiently proceed even at the polymerization temperature of not higher than 300° C.

[Chem. 6]

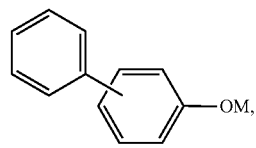

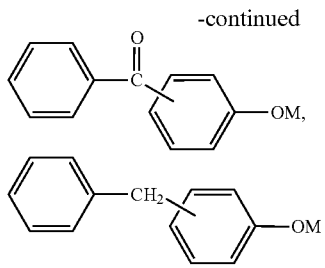

Herein M in these formulae represents at least one species selected among Li, Na, K and Cs.

Any of these metal alkoxides and/or metal phenoxides may be used alone, or two or more of these metal alkoxides and/or metal phenoxides may be used as a mixture. Performing the thermal ring-opening polymerization of the cyclic poly(phenylene ether ether ketone) in the presence of any of these metal alkoxides and/or metal phenoxides enables the poly (phenylene ether ether ketone) to be obtained in a short time and additionally enables production of the poly(phenylene ether ether ketone) substantially free from foreign matter resulting from the above cross-linking reactions and decomposition reactions. The presence or the absence of the foreign matter resulting from the above cross-linking reactions and decomposition reactions and the amount of the resulting foreign matter are respectively determined as the presence or the absence of any insoluble matter in 98% by weight of concentrated sulfuric acid and the amount of the insoluble matter in the course of mixing the obtained poly(phenylene ether ether ketone) with 98% by weight of concentrated sulfuric acid at the concentration of 10 mg/mL at room temperature.

The amount of the metal alkoxide and/or the metal phenoxide used differs according to the molecular weight of the target poly(phenylene ether ether ketone) and the types of the metal alkoxide and/or the metal phenoxide, but, in general, preferably not less than 0.001 mol % relative to 1 mol of a repeating unit defined by a formula —(O-Ph-O-Ph-CO-Ph)- which is the primary structural unit of the cyclic poly(phenylene ether ether ketone), is more preferably not less than 0.005 mol %, is furthermore preferably not less than 0.01 mol %, is especially preferably not less than 0.05 mol % and is more especially preferably not less than 0.1 mol %. The amount of the above metal alkoxide and/or the metal phenoxide used is also preferably not greater than 50 mol % relative to 1 mol of the above repeating unit, is more preferably not greater than 20 mol %, is furthermore preferably not greater than 15 mol %, is especially preferably not greater than 10 mol % and is more especially preferably not greater than 5 mol %. Addition of the metal alkoxide and/or the metal phenoxide in this preferable range enables the thermal ring-opening polymerization of the cyclic poly(phenylene ether ether ketone) to proceed in a short time and also facilitates sufficient high polymerization.

The procedure of adding any of these metal alkoxides and/or metal phenoxides may be simple addition, but it is preferable to add the metal alkoxide and/or the metal phenoxide to the cyclic poly(phenylene ether ether ketone) composition and then homogeneously disperse the added metal alkoxide and/or metal phenoxide. For example, a method of mechanical dispersion or a dispersion method using a solvent may be employed as the method of homogeneously dispersing the metal alkoxide and/or the metal phenoxide. The method of mechanical dispersion may be specifically a method that uses a pulverizer, a stirrer, a mixer, a shaker or a mortar. The dispersion method using the solvent may be specifically a method that dissolves or disperses the cyclic poly(phenylene ether ether ketone) composition in an adequate solvent, adds the metal alkoxide and/or the metal phenoxide to the solution or the fluid dispersion to be dissolved or dispersed and subsequently removes the solvent. When the metal alkoxide and/or the metal phenoxide is in a solid form, the average particle diameter of the metal alkoxide and/or the metal phenoxide is preferably not greater than 1 mm, in order to enable more homogeneous dispersion.

In the course of the thermal ring-opening polymerization of the cyclic poly(phenylene ether ether ketone) in the cyclic poly(phenylene ether ether ketone) composition according to the embodiment of the invention, a compound expressed by a formula $R^2$—X may further be added as an additive. $R^2$ represents an aliphatic group containing 1 to 20 carbons or an aromatic group containing 6 to 30 carbon atoms, and the aromatic ring may include an alkyl group, a phenyl group or another heteroatom-containing substituent group. X represents an electron-withdrawing leaving group. Preferable examples of the electron-withdrawing leaving group include halogen atoms, nitro group, azide group, cyano group, carboxyl group, acetyl group, acylamino group, sulfonamide group, sulfamoyl group, carbamoyl group, sulfo group and quaternary ammonium group. Especially preferable are halogen atoms, nitro group, cyano group, carboxyl group and acetyl group, and more preferable are halogen atoms.

Concrete examples of the compound expressed by the formula $R^2$—X include fluoromethane, chloromethane, bromomethane, iodomethane, fluoroethane, chloroethane, bromoethane, iodoethane, n-butyl fluoride, n-butyl chloride, n-butyl bromide, n-butyl iodide, s-butyl fluoride, s-butyl chloride, s-butyl bromide, s-butyl iodide, t-butyl fluoride, t-butyl chloride, t-butyl bromide, t-butyl iodide, n-propyl fluoride, n-propyl chloride, n-propyl bromide, n-propyl iodide, isopropyl fluoride, isopropyl chloride, isopropyl bromide, isopropyl iodide, cyclohexyl fluoride, cyclohexyl chloride, cyclohexyl bromide, cyclohexyl iodide, fluorobenzene, chlorobenzene, bromobenzene, iodobenzene, 4-phenylfluorobenzene, 4-phenylchlorobenzene, 4-phenylbromobenzene, 4-phenyliodobenzene, 4-phenoxyfluorobenzene, 4-phenoxychlorobenzene, 4-phenoxybromobenzene, 4-phenoxyiodobenzene, 4-fluorobenzophenone, 4-chlorobenzophenone, 4-bromobenzophenone, 4-iodobenzophenone, 2-benzylfluorobenzene, 2-benzylchlorobenzene, 2-benzylbromobenzene, 2-benzyliodobenzene, 4-benzylfluorobenzene, 4-benzylchlorobenzene, 4-benzylbromobenzene and 4-benzyliodobenzene.

The amount of the additive used differs according to the molecular weight of the target poly(phenylene ether ether ketone) and the type of the additive, but may be generally not less than 0.001 mol % relative to 1 mol of the repeating unit defined by the formula —(O-Ph-O-Ph-CO-Ph)- which is the primary structural unit of the cyclic poly(phenylene ether ether ketone), is preferably not less than 0.005 mol %, is more preferably not less than 0.01 mol % and is furthermore preferably not less than 0.05 mol %. The amount of the additive used may be not greater than 50 mol % relative to 1 mol of the above repeating unit, is preferably not greater than 20 mol %, is more preferably not greater than 15 mol % and is furthermore preferably not greater than 10 mol %. Addition of the amount of the additive in this preferable range facilitates control of the molecular weight of the poly(phenylene ether ether ketone) and the molecular weight distribution to desired ranges.

The procedure of adding any of these additives may be simple addition, but it is preferable to add the additive to the cyclic poly(phenylene ether ether ketone) composition and then homogeneously disperse the added additive. For example, a method of mechanical dispersion or a dispersion method using a solvent may be employed as the method of homogeneously dispersing the additive. The method of mechanical dispersion may be specifically a method that uses a pulverizer, a stirrer, a mixer, a shaker or a mortar. The dispersion method using the solvent may be specifically a method that dissolves or disperses the cyclic poly(phenylene ether ether ketone) composition in an adequate solvent, adds the additive to the solution or the fluid dispersion to be dissolved or dispersed and subsequently removes the solvent. When the additive is in a solid from, the average particle diameter of the additive is preferably not greater than 1 mm, in order to enable more homogeneous dispersion.

Even in the case of addition of the above additive, the production method of the poly(phenylene ether ether ketone) according to the embodiment of the invention can lower the heating temperature that ensures sufficiently high polymerization, since the melting point of the cyclic poly(phenylene ether ether ketone) composition used is as low as 270° C. or below.

The thermal ring-opening polymerization of the cyclic poly(phenylene ether ether ketone) in the cyclic poly(phenylene ether ether ketone) composition may be performed in a solvent or under a condition substantially free from a solvent. Especially preferable is to perform under the condition substantially free from the solvent, since this enables a temperature rise in a short time, a high reaction rate and production of the poly(phenylene ether ether ketone) in a short time. The condition substantially free from the solvent herein indicates that the content of the solvent in the cyclic poly(phenylene ether ether ketone) composition is not higher than 20% by weight, is preferably not higher than 10% by weight and is more preferably not higher than 5% by weight.

The atmosphere in the thermal ring-opening polymerization of the cyclic poly(phenylene ether ether ketone) in the cyclic poly(phenylene ether ether ketone) composition is not specifically limited but is preferably a non-oxidizing atmosphere. It is also preferable to perform the thermal ring-opening polymerization under a reduced pressure condition. When the thermal ring-opening polymerization is performed under the reduced pressure condition, it is preferable to achieve the reduced pressure condition after once controlling the atmosphere in the reaction system to the non-oxidizing atmosphere. This reduces the occurrence of undesired side reactions, for example, cross-linking reactions between the cyclic poly(phenylene ether ether ketone)s, between the resulting poly(phenylene ether ether ketone)s and between the resulting poly(phenylene ether ether ketone) and the cyclic poly(phenylene ether ether ketone), and decomposition reactions. The non-oxidizing atmosphere herein indicates an atmosphere that has the oxygen concentration of not higher than 5% by volume, preferably has the oxygen concentration of not higher than 2% by volume or more preferably does not substantially contain oxygen, in a gas phase, to which the cyclic poly(phenylene ether ether ketone) is exposed, and is more specifically, for example, an inert gas atmosphere such as nitrogen, helium or argon. Among them, nitrogen atmosphere is especially preferable in terms of the economical efficiency and the easiness of handling. The reduced pressure condition herein indicates that the pressure in the reaction system is lower than the atmospheric pressure. The upper limit of the pressure is preferably not greater than 50 kPa, is more preferably not greater than 20 kPa and is furthermore preferably not greater than 10 kPa. The lower limit may be not less than 0.1 kPa and is more preferably not less than 0.2 kPa. Under the reduced pressure condition of the desired lower limit or above, cyclic compounds of low molecular weights included in the cyclic poly(phenylene ether ether ketone) composition are unlikely to be vaporized. Under the reduced pressure condition of the desired upper limit or below, on the other hand, the undesired side reactions such as the cross-linking reactions are unlikely to occur.

The heating method is not specifically limited but may be any method that uses any device equipped with a heating mechanism; for example, a method using a mold used for production of a molded product or a method using an extruder or a melt kneader, as well as a method using a conventional polymerization reactor. Any known technique, for example, a batch system or a continuous system may be employed for heating.

The reduced viscosity ($\eta$) of the poly(phenylene ether ether ketone) obtained by the production method according to the embodiment of the invention is preferably not less than 0.2 dL/g, is more preferably not less than 0.3 dL/g and is furthermore preferably not less than 0.6 dL/g. The reduced viscosity ($\eta$) is also preferably not higher than 2.5 dL/g, is more preferably not higher than 2.0 dL/g and is furthermore preferably not higher than 1.8 dL/g. Controlling the reduced viscosity of the resulting poly(phenylene ether ether ketone) to the above preferable range is likely to achieve the high molding processability and the good mechanical properties and chemical resistance of a molded product.

The intrinsic viscosity ($[\eta]$) of the poly(phenylene ether ether ketone) is not less than 0.10 dL/g, is preferably not less than 0.20 dL/g, is more preferably not less than 0.30 dL/g, is furthermore preferably not less than 0.56 dL/g and is especially preferably not less than 0.60 dL/g. The intrinsic viscosity ($[\eta]$) is also not higher than 2.50 dL/g, is preferably not higher than 2.00 dL/g and is more preferably not higher than 1.80 dL/g. The intrinsic viscosity of the poly(phenylene ether ether ketone) that is less than 0.10 dL/g is not preferable, since this poly(phenylene ether ether ketone) has an insufficient degree of polymerization and does not have properties which are supposed to be achieved for the poly(phenylene ether ether ketone). The intrinsic viscosity that exceeds 2.50 dL/g is not preferable, on the other hand, since the poor flowability in melting causes difficulty in molding process.

Unless otherwise specified, the reduced viscosity according to the embodiment of the invention indicates a value measured by using an Ostwald viscosimeter at 25° C. immediately after completion of dissolution in a concentrated sulfuric acid solution having a concentration of 0.1 g/dL (weight of poly(phenylene ether ether ketone)/volume of 98% by weight of concentrated sulfuric acid). The calculation of the reduced viscosity follows an equation given below:

$$\eta = \{(t/t0) - 1\}/C$$

(wherein t represents the number of seconds when the sample solution passes through, t0 represents the number of seconds when the solvent (98% by weight of concentrated sulfuric acid) passes through, and C represents the concentration of the solution).

Unless otherwise specified, the intrinsic viscosity indicates a value obtained by preparing two or more concentrated sulfuric acid solutions of different concentrations, measuring the values $\eta$ of the respective concentrated sulfuric acid solutions under the same conditions as those of the above reduced viscosity and extrapolating C of the above equation to 0.

The melting point of the sufficiently polymerized poly(phenylene ether ether ketone) is known to be generally not lower than 320° C. The high heat resistance attributed to this high melting point is one characteristic of the poly(phenylene ether ether ketone). It is accordingly preferable that the melting point of the resulting poly(phenylene ether ether ketone) is not lower than 320° C. The melting point of lower than 320° C. is not preferable, since this suggests insufficiently high polymerization or the possibility of the occurrence of the undesired side reactions and additionally fails to give the properties of the poly(phenylene ether ether ketone) which are supposed to be achieved.

The number-average molecular weight (Mn) of the resulting poly(phenylene ether ether ketone) according to the embodiment of the invention is preferably not less than 2.0 thousands, is more preferably not less than 5.0 thousands and is furthermore preferably not less than 10.0 thousands. The above number-average molecular weight (Mn) is also preferably not greater than 3000 thousands, is preferably not greater than 1500 thousands and is furthermore preferably not greater than 300 thousands. Controlling the number-average molecular weight to this preferable range is likely to achieve the high molding processability and the good mechanical properties and chemical resistance of a molded product. The polydispersity (Mw/Mn) expressed as the ratio of the weight-average molecular weight (Mw) to the number-average molecular weight (Mn) is preferably not less than 1.0. The polydispersity (Mw/Mn) is also preferably not greater than 10.0, is more preferably not greater than 5.0 and is furthermore preferably not greater than 4.0. Controlling the polydispersity to this preferable range is likely to obtain a homogeneous poly(phenylene ether ether ketone) molded product. The values Mw, Mn and Mw/Mn of the resulting poly(phenylene ether ether ketone) according to the embodiment of the invention may be measured by gel permeation chromatography (GPC). More specifically, after modification of the poly(phenylene ether ether ketone) by the technique described in Macromolecules, volume 42, page 1955 (2009), these values may be measured as values of polystyrene equivalent by a GPC measurement device equipped with a differential refractometer detector.

Employing the production method according to the embodiment of the invention for production of the poly(phenylene ether ether ketone) enables production of poly(phenylene ether ether ketone) having a structural unit selected between an alkoxy structural unit and a phenoxy structural unit in at least one terminal structure. This is because nucleophilic attack on the cyclic poly(phenylene ether ether ketone) by the metal alkoxide and/or the metal phenoxide starts an initiation reaction and enables ring-opening polymerization to proceed. The alkoxy structural unit or the phenoxy structural unit of this poly(phenylene ether ether ketone) is linked with the end of the molecular chain of the poly(phenylene ether ether ketone) via an oxygen atom contained in either of these structural units. In other words, when the alkoxy structural unit or the phenoxy structural unit is expressed as $R^1O$, the poly(phenylene ether ether ketone) obtained is expressed by General Formula (III) given below:

[Chem. 7]

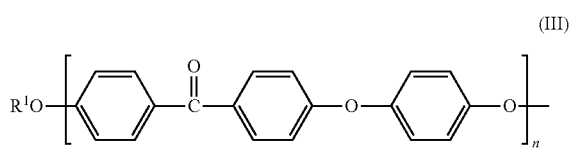

(III)

In this formula, n represents an integer of not less than 2, and $R^1$ represents either an aliphatic group or aromatic group containing 1 to 20 carbon atoms.

The presence of the structural end selected between the alkoxy structural unit and the phenoxy structural unit in at least one terminal structure of the poly(phenylene ether ether ketone) advantageously facilitates reduction in amount of the reactive terminal group in the polymer, interference with the progress of side reactions and improvement of the thermal stability. The above poly(phenylene ether ether ketone) may further include poly(phenylene ether ether ketone) expressed by General Formula (IV) given below:

[Chem. 8]

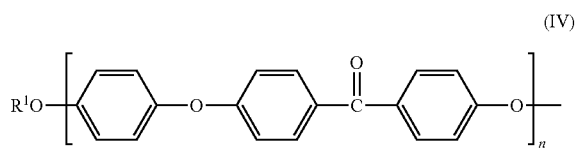

(IV)

In this formula, n represents an integer of not less than 2, and $R^1$ represents either an aliphatic group or aromatic group containing 1 to 20 carbon atoms.

The production method according to the embodiment of the invention employed for production of poly(phenylene ether ether ketone) enables production of poly(phenylene ether ether ketone) having a structure expressed by —$OR^2$ derived from an additive in at least one terminal structure. This is because the electron-withdrawing leaving group of the additive reacts with an anionic group at the end of the molecular chain of the poly(phenylene ether ether ketone). Accordingly the poly(phenylene ether ether ketone) obtained is expressed by General Formula (V) given below:

[Chem. 9]

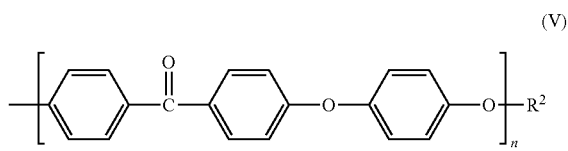

(V)

In this formula, n represents an integer of not less than 2, and $R^2$ represents either an aliphatic group containing 1 to 20 carbon atoms or an aromatic group containing 6 to 30 atoms, wherein the aromatic ring may include an alkyl group, a phenyl group or another heteroatom-containing substituent group.

The presence of the structure expressed by —$OR^2$ derived from the additive in at least one reactive terminal group of the poly(phenylene ether ether ketone) facilitates the control of the molecular weight and the molecular weight distribution to desired ranges. The above poly(phenylene ether ether ketone) may further include poly(phenylene ether ether ketone) expressed by General Formula (VI) given below:

[Chem. 10]

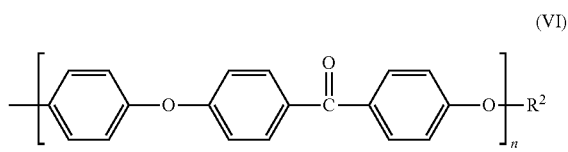

(VI)

In this formula, n represents an integer of not less than 2, and $R^2$ represents either an aliphatic group containing 1 to 20 carbon atoms or an aromatic group containing 6 to 30 atoms, wherein the aromatic ring may include an alkyl group, a phenyl group or another heteroatom-containing substituent group.

The production method according to the embodiment of the invention employed for production of poly(phenylene ether ether ketone) also enables production of poly(phenylene ether ether ketone) having a structural unit selected between an alkoxy structural unit and a phenoxy structural unit in one terminal structure and a structure expressed by —$OR^2$ derived from an additive and expressed by General Formula (VII) given below in the other terminal structure. When a metal alkoxide and/or a metal phenoxide and the above additive are added to a composition including a cyclic poly(phenylene ether ether ketone), ring-opening polymerization of the cyclic poly(phenylene ether ether ketone) is triggered by the metal alkoxide and/or the metal phenoxide. As described above, the molecular chain obtained by the ring-opening polymerization accordingly has a structure including —$R^1O$ derived from the metal alkoxide and/or the metal phenoxide at one end and an anionic group at the other end. The anionic group then reacts with the electron-withdrawing leaving group of the additive. The resulting poly(phenylene ether ether ketone) accordingly has —$OR^1$ at one end and —$OR^2$ derived from the additive at the other end.

[Chem. 11]

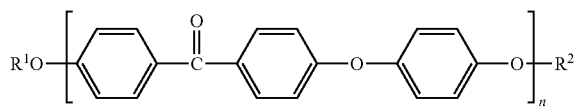

(VII)

In this formula, n represents an integer of not less than 2, $R^1$ represents either an aliphatic group or aromatic group containing 1 to 20 carbon atoms, and $R^2$ represents either an aliphatic group containing 1 to 20 carbon atoms or an aromatic group containing 6 to 30 atoms. The aromatic ring may include an alkyl group, a phenyl group or another heteroatom-containing substituent group, and $R^1$ and $R^2$ may be the same or may be different.

The presence of the structural unit selected between the alkoxy structural unit and the phenoxy structural unit in one terminal structure of the poly(phenylene ether ether ketone) and the structure expressed by —$OR^2$ derived from the additive in the other terminal structure facilitates reduction in amount of the reactive terminal group in the polymer, interference with the progress of side reactions and improvement of the thermal stability, as well as facilitates the control of the molecular weight and the molecular weight distribution to desired ranges. The above poly(phenylene ether ether ketone) may further include poly(phenylene ether ether ketone) expressed by General Formula (VIII) given below:

[Chem. 12]

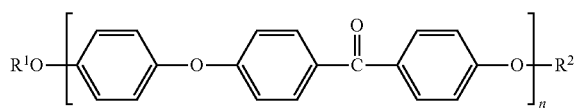

(VIII)

In this formula, n represents an integer of not less than 2, $R^1$ represents either an aliphatic group or aromatic group containing 1 to 20 carbon atoms, and $R^2$ represents either an aliphatic group containing 1 to 20 carbon atoms or an aromatic group containing 6 to 30 atoms. The aromatic ring may include an alkyl group, a phenyl group or another heteroatom-containing substituent group, and $R^1$ and $R^2$ may be the same or may be different.

After modification of poly(phenylene ether ether ketone) by the technique described in Macromolecules, volume 42, page 1955 (2009), the modified poly(phenylene ether ether ketone) is dissolved in deuterated chloroform and is subjected to proton nuclear magnetic resonance (NMR) spectroscopy. This identifies the end derived from the metal alkoxide or the metal phenoxide and expressed by —$OR^1$ of General Formulae (III) to (VIII) given above and the end derived from the additive and expressed by —$OR^2$ and determines their abundance ratios in the polymer ends from their peak area intensity ratios.

The thermal ring-opening polymerization of the cyclic poly(phenylene ether ether ketone) according to the embodiment of the invention may be performed in the coexistence of a fibrous substance. The fibrous substance herein indicates a fine threadlike substance and is preferably any substance having an elongated structure like natural fibers. A composite material structure including poly(phenylene ether ether ketone) and the fibrous material can be readily produced by converting the cyclic poly(phenylene ether ether ketone) into the poly(phenylene ether ether ketone) in the presence of the fibrous substance. This structure is reinforced by the fibrous substance and accordingly has, for example, excellent mechanical properties, compared with the poly(phenylene ether ether ketone) alone.

Among various fibrous substances, it is preferable to use long-staple reinforcing fibers. This enables production of highly-reinforced poly(phenylene ether ether ketone). In general, in the case of production of a composite material structure including a resin and a fibrous substance, the high melt viscosity of the resin often causes the poor wettability of the resin with the fibrous substance and thereby fails to production of a homogeneous composite material or to achieve expected mechanical properties. The wettability herein means that a fluid substance such as a melt resin and a solid substrate such as a fibrous compound maintain a good physical contact in order to prevent the air or another gas from being substantially trapped between the fluid substance and the solid substrate. Here the lower viscosity of the fluid substance results in the better wettability with the fibrous substance. The cyclic poly(phenylene ether ether ketone) included in the cyclic poly(phenylene ether ether ketone) composition according to the embodiment of the invention has the remarkably lower melt viscosity than those of general thermoplastic resins, for example, conventionally known cyclic poly(phenylene ether ether ketone) of the higher melting point and is thereby likely to have the good wettability with the fibrous substance. According to the production method of poly(phenylene ether ether ketone) of the embodiment of the invention, after achievement of the good wettability between the fibrous substance and the cyclic poly(phenylene ether ether ketone) in the cyclic poly(phenylene ether ether ketone) composition, the cyclic poly(phenylene ether ether ketone) is converted into poly(phenylene ether ether ketone). This readily produces a complex material structure having the good wettability of the poly(phenylene ether ether ketone) with the fibrous substance.

The fibrous substance is preferably the long-staple reinforcing fibers as described above. The reinforcing fibers used according to the invention are not specifically limited, but preferably used reinforcing fibers are fibers of good heat resistance and good tensile strength generally used as high-performance reinforcing fibers. Examples of such reinforcing fibers include glass fibers, carbon fibers, graphite fibers, aramid fibers, silicon carbide fibers, alumina fibers and boron fibers. Among them, most preferable are carbon fibers and graphite fibers having good specific strength and good specific modulus and significant contribution to weight reduction. As the carbon fibers and the graphite fibers, any types of carbon fibers and graphite fibers may be used according to their applications, but most suitable are carbon fibers of high strength and high ductility having the tensile strength of 450 Kgf/mm2 and the tensile ductility of not lower than 1.6%. When the long-staple reinforcing fibers are used, their length is preferably not shorter than 5 cm. The length of this range readily enables the strength of the reinforcing fibers to be sufficiently provided to the composite material. The carbon fibers or graphite fibers may be mixed with other reinforcing fibers. The shape and the array of the reinforcing fibers are not limited, but the reinforcing fibers may be, for example, unidirectional fibers, random-directional fibers, sheet-like fibers, mat-like fibers, fibrous fibers or braid-like fibers. The reinforcing fibers having the unidirectionally adjusted array are most suitable for applications that need the specifically high specific strength and specific modulus. The easily-handled cloth-like (fabric-like) array is also suitable for the embodiment of the invention.

The above conversion of the cyclic poly(phenylene ether ether ketone) in the cyclic poly(phenylene ether ether ketone) composition into poly(phenylene ether ether ketone) may be performed in the presence of a filler. The filler may be, for example, non-fibrous glass, non-fibrous carbon, or an inorganic filler such as calcium carbonate, titanium oxide or alumina.

The poly(phenylene ether ether ketone) obtained as described above may be molded and used in various applications, for example, automobile components, electric and electronic components, building materials and various vessels, as well as fibers, sheets, films and pipes by any of general molding techniques, such as injection molding, injection compression molding, blow molding, extrusion molding and press molding.

EXAMPLES

The following describes the invention more specifically with reference to examples. These examples are, however, only illustrative and not restrictive.

Various physical properties are measured by high-performance liquid chromatography, a differential scanning calorimeter (DSC), an infrared spectrometer (IR) and an Ostwald viscosimeter. The quantitative analysis of cyclic poly(phenylene ether ether ketone) is performed by high-performance liquid chromatography. The detailed conditions of analysis are given below.

<Content and Composition of Cyclic Poly(Phenylene Ether Ether Ketone)>

The content of a cyclic poly(phenylene ether ether ketone) mixture (mixture of cyclic poly(phenylene ether ether ketone)s having different integers m) in a cyclic poly(phenylene ether ether ketone) composition and the composition of the cyclic poly(phenylene ether ether ketone) mixture were measured by high-performance liquid chromatography under the following conditions:

Apparatus: LC-10Avp series manufactured by SHIMADZU CORPORATION;
Column: Mightysil RP-18GP150-4.6;
Detector: photodiode array detector (using UV=270 nm);
Column Temperature: 40° C.;
Sample Concentration: 0.02% by weight tetrahydrofuran (THF) solution; and
Mobile Phase: THF/0.1% by weight of trifluoroacetic acid solution <Thermal Properties>

The thermal properties of the obtained polymer were measured under nitrogen atmosphere by using a robot DSC RDC220 manufactured by Seiko Instruments Inc. The following measurement conditions were employed, and the value of an endothermic peak in Second Run was used as the melting point of cyclic poly(phenylene ether ether ketone) and the value of an endothermic peak in First Run was used as the melting point of poly(phenylene ether ether ketone):

(First Run)
maintained at 50° C.×1 minute;
raised temperature from 50° C. to 380° C. at the temperature rise rate of 20° C./minute; and
maintained at the raised temperature×1 minute
(Second Run)
maintained at 50° C.×1 minute; and
raised temperature from 50° C. to 380° C. at the temperature rise rate of 20° C./minute <Qualitative Analysis>

The qualitative analysis of the obtained compound was performed using an infrared spectrometer. The following method was employed for sample preparation.

Apparatus: Perkin Elmer System 2000 FT-IR; and
Sample Preparation: KBr method

<Measurement of Reduced Viscosity>

Viscosimeter: Ostwald viscosimeter;
Solvent: 98% by weight sulfuric acid;
Sample Concentration: 0.1 g/dL (weight of sample/volume of solvent);
Measurement Temperature: 25° C.;
Calculation Formula of Reduced Viscosity: $\eta=\{(t/t0)-1\}/C$;
t: the number of seconds when the sample solution passes through;
t0: the number of seconds when the solvent passes through; and
C: the concentration of the solution <Calculation of Intrinsic Viscosity>

The intrinsic viscosity was calculated by the following method. Concentrated sulfuric acid solutions were prepared under the same conditions as the above measurement conditions of the reduced viscosity, except that the concentrations of the sample solutions were adjusted to 0.1, 0.5, 1.0 and 2.0 g/dL, and the values $\eta$ at the respective concentrations were calculated according to the above calculation formula of the reduced pressure. The calculated value $\eta$ (y axis) was plotted against the concentration C of the sample solution (x axis). A straight line obtained was extrapolated to C→0, and the resulting value was provided as the intrinsic viscosity.

<Terminal Structure of Poly(Phenylene Ether Ether Ketone)>

The terminal structure of the obtained poly(phenylene ether ether ketone) was measured and identified by proton nuclear magnetic resonance (NMR) spectroscopy:

Apparatus: 500 MHz-NMR manufactured by JEOL Ltd.;
Solvent: deuterated chloroform; and
Sample Concentration: 1 mg/mL <Molecular Weight Distribution of Poly(Phenylene Ether Ether Ketone)>

With respect to the molecular weight of the obtained poly (phenylene ether ether ketone), the number-average molecular weight (Mn) and the weight-average molecular weight (Mw) in poly(methyl methacrylate) equivalent were measured by gel permeation chromatography (GPC), which is one type of size exclusion chromatography (SEC), and the polydispersity (Mw/Mn) was calculated. The measurement conditions of GPC are shown below:

Apparatus: System Controller: CBM-20A manufactured by SHIMADZU CORPORATION;
Differential Refractometer Detector: RID-10A manufactured by SHIMADZU CORPORATION;
Pump: LC-20AD manufactured by SHIMADZU CORPORATION;
Column: Shodex KF806;
Eluent tetrahydrofuran;
Detector: differential refractometer detector;
Column Temperature: 40° C.;
Flow Rate: 1.0 mL/min;
Sample Injection Volume: 100 μL; and
Sample Concentration: 0.1 mg/mL <Check for Foreign Matter>

The presence or the absence of any foreign matter in the obtained poly(phenylene ether ether ketone) was checked by the following procedure, The procedure mixed 25 mg of the obtained poly(phenylene ether ether ketone) with 98% by weight of concentrated sulfuric acid at the concentration of 10 mg/mL and was kept at room temperature under stirring for 12 hours. The procedure then visually checked for the presence or the absence of any insoluble matter (foreign matter) in 98% by weight of concentrated sulfuric acid.

Reference Example 1

Production of Cyclic Poly(Phenylene Ether Ether Ketone) Composition (A-1)

In a 1-liter autoclave equipped with a stirrer, 10.91 g (50 mmol) of 4,4'-difluorobenzophenone, 5.51 g (50 mmol) of hydroquinone, 6.91 g (50 mmol) of potassium carbonate anhydride and 500 mL of N-methyl-2-pyrrolidone were mixed. The amount of N-methyl-2-pyrrolidone relative to 1.0 mol of the benzene ring component in the mixture was 3.33 liters.

After the reaction vessel was sealed under nitrogen gas at room temperature and ordinary pressure, the reaction was performed with stirring at 400 rpm by heating from room temperature to 140° C., maintaining at 140° C. for 1 hour, subsequently heating to 180° C., maintaining at 180° C. for 3 hours, subsequently heating to 230° C. and maintaining at 230° C. for 5 hours. On completion of the reaction, the reaction vessel was cooled down to room temperature and a reaction product was obtained.

About 0.2 g of the obtained reaction product was weighed and diluted with about 4.5 g of THF. A sample of high-performance liquid chromatography was prepared by separation removal of a THF insoluble component by filtration and was subjected to analysis of the reaction product. As a result of the analysis, production of seven different cyclic poly(phenylene ether ether ketone)s having consecutive repeating numbers m=2 to 8 was confirmed. The yield of the cyclic poly(phenylene ether ether ketone) mixture relative to hydroquinone was 11.5%.

A 50 g aliquot of this obtained reaction product was mixed with 150 g of 1% by weight of an acetic acid aqueous solution and was slurried by stirring. The slurry was then heated to 70° C. and was continuously stirred for 30 minutes. A solid substance was obtained by filtering the slurry through a glass filter (mean pore size of 10 to 16 μm). A series of operations of dispersing the obtained solid substance in 50 g of deionized water, maintaining the dispersion at 70° C. for 30 minutes and filtering the dispersion to obtain a solid substance was repeated three times. The resulting solid substance was vacuum dried overnight at 70° C., and about 1.24 g of a dried solid matter was obtained.

Subsequently, 1.0 g of the dried solid matter obtained above was subjected to Soxhlet extraction using 100 g of chloroform at the bath temperature of 80° C. for 5 hours. Chloroform was removed from the resulting extract by using an evaporator, and a solid substance was obtained. A dispersion was prepared by using an ultrasonic cleaner after addition of 2 g of chloroform to this solid substance and was subsequently added dropwise to 30 g of methanol. A precipitate obtained by this process was filtered through filter paper having the mean pore size of 1 μm and was subsequently vacuum dried at 70° C. for 3 hours. A cyclic poly(phenylene ether ether ketone) composition (A-1) was then obtained as a white solid matter. The amount of the obtained white solid matter was 0.11 g, and the yield of the white solid matter relative to hydroquinone used for the reaction was 11.3%.

The powder of this cyclic poly(phenylene ether ether ketone) composition (A-1) was identified as a compound having phenylene ether ketone units from absorption spectra by infrared spectroscopy. By analysis of high-performance liquid chromatography, it was identified that seven different cyclic poly(phenylene ether ether ketone)s having consecutive repeating numbers m=2 to 8 (cyclic poly(phenylene ether ether ketone) mixture) were included in the cyclic poly(phenylene ether ether ketone) composition (A-1). This analysis also showed that the content of the cyclic poly(phenylene ether ether ketone) mixture in the cyclic poly(phenylene ether ether ketone) composition (A-1) was 85% by weight. A component other than cyclic poly(phenylene ether ether ketone)s in the cyclic poly(phenylene ether ether ketone) composition (A-1) was linear poly(phenylene ether ether ketone) oligomer.

The melting point of this cyclic poly(phenylene ether ether ketone) composition (A-1) was measured to be 159° C. The reduced viscosity was less than 0.02 dL/g.

Reference Example 2

Production of Cyclic Poly(Phenylene Ether Ether Ketone) Composition (A-2)

In a 2-liter four-necked flask equipped with a condenser tube, a Dean-Stark apparatus and a nitrogen blowing tube, 66.07 g (600 mmol) of hydroquinone, 91.22 g (660 mmol) of potassium carbonate, 500 mL of dimethylacetamide and 260 mL of toluene were mixed. The mixture was heated to 120° C. with stirring under nitrogen stream and was refluxed for 4 hours for removal of the solvent and the water content in the raw materials. The reaction solution was cooled down to room temperature and was subsequently heated at 135° C. for 24 hours after addition of 6.55 g (30 mmol) of 4,4'-difluorobenzophenone for removal of toluene. The reaction solution was kept heated for another 5 hours, was subsequently cooled down to room temperature and was added dropwise to 2.5 L of water. The resulting solid substance was filtered through filter paper having the mean pore size of 1 and was vacuum dried at 80° C. for 12 hours. The resulting dried solid matter was subjected to Soxhlet extraction using acetone for 6 hours. The acetone solution was further purified by a silica gel column (eluent: hexane/ethyl acetate=1.5/1), and 10.54 g of 4,4'-bis(4-hydroxyphenoxy)benzophenone was obtained.

In a 1-liter four-necked flask equipped with a condenser tube, a nitrogen blowing tube and a Dean-Stark apparatus, on the other hand, 150 mL of dimethylacetamide and 78 mL of toluene were mixed, were heated at 120° C. for 4 hours to remove water included in the solvent and were subsequently heated at 135° C. for 24 hours to distill out toluene. Subsequently, 0.654 g (36 mmol) of potassium carbonate was added to the mixture, and 1.195 g (3.0 mmol) of the above 4,4'-bis (4-hydroxyphenoxy)benzophenone and 1.520 g (3.0 mmol) of 1,4-bis(4-(4-fluorobenzoyl)phenoxy)benzene were added in four parts in 36 hours. After addition of the entire amount, the reaction further proceeded for 65 hours. The reaction solution was concentrated by an evaporator, and the fluid concentrate was added dropwise to water. After removal of the precipitate by filtration, the filtrate was collected and dried, so that 0.844 g of dried solid matter was obtained. This dried solid matter was further subjected to Soxhlet extraction using chloroform for 6 hours, and 0.809 g of a cyclic poly (phenylene ether ether ketone) composition (A-2) was then obtained as a white solid matter.

About 2 mg of the obtained cyclic poly(phenylene ether ether ketone) composition (A-2) was weighed and diluted with 10 g of THF. A sample of high-performance liquid chromatography was prepared by separation removal of a THF insoluble component by filtration, and the cyclic poly (phenylene ether ether ketone) composition (A-2) was analyzed. As a result of the analysis, production of two different cyclic poly(phenylene ether ether ketone)s having repeating numbers m=3 and 6 (cyclic poly(phenylene ether ether ketone) mixture) was confirmed. This analysis also showed that the content of the cyclic poly(phenylene ether ether ketone) mixture in the cyclic poly(phenylene ether ether ketone) composition (A-2) was 94% by weight.

The powder of this cyclic poly(phenylene ether ether ketone) composition (A-2) was identified as a compound having phenylene ether ketone units from absorption spectra by infrared spectroscopy.

The melting point of this cyclic poly(phenylene ether ether ketone) composition (A-2) was measured to be 275° C. Additionally, the reduced viscosity of this cyclic poly(phenylene ether ether ketone) composition (A-2) was measured to be less than 0.02 dL/g.

Example 1

Production of Poly(Phenylene Ether Ether Ketone)

After 200 mg of a powder mixture of the cyclic poly(phenylene ether ether ketone) composition (A-1) obtained in Reference Example 1 with potassium 4-phenylphenoxide (B-1) as a polymerization initiator was placed in a glass ampoule bottle, the inside of the ampoule bottle was substituted with nitrogen. The mixing ratio of this polymerization initiator (B-1) was 5 mol % relative to the repeating unit expressed by a formula —(O-Ph-O-Ph-CO-Ph)-, which is the primary structural unit of the cyclic poly(phenylene ether ether ketone). The ampoule bottle was placed in an electric oven at the temperature controlled to 280° C., was heated for 30 minutes and was subsequently taken out of the electric oven to be cooled down to room temperature. A black solid matter was then obtained.

The result of analysis using a differential scanning calorimeter showed that the black solid matter had the melting point of 340° C. It was also shown that the black solid matter was fully dissolved in 98% by weight of concentrated sulfuric acid and had the reduced viscosity of 0.60 dL/g and the intrinsic viscosity of 0.60 dL/g.

Example 2

Production of Poly(Phenylene Ether Ether Ketone)

After 200 mg of a powder mixture of the cyclic poly(phenylene ether ether ketone) composition (A-1) obtained in Reference Example 1 with potassium 4-phenylphenoxide (B-1) as a polymerization initiator was placed in a glass ampoule bottle, the inside of the ampoule bottle was substituted with nitrogen. The mixing ratio of this polymerization initiator (B-1) was 5 mol % relative to the repeating unit expressed by a formula —(O-Ph-O-Ph-CO-Ph)-, which is the primary structural unit of the cyclic poly(phenylene ether ether ketone). The ampoule bottle was placed in an electric oven at the temperature controlled to 300° C., was heated for 30 minutes and was subsequently taken out of the electric oven to be cooled down to room temperature. A black solid matter was then obtained.

The result of analysis using a differential scanning calorimeter showed that the black solid matter had the melting point of 341° C. It was also shown that the black solid matter was fully dissolved in 98% by weight of concentrated sulfuric acid and had the reduced viscosity of 0.70 dL/g and the intrinsic viscosity of 0.69 dL/g.

Example 3

Production of Poly(Phenylene Ether Ether Ketone)

After 200 mg of a powder mixture of the cyclic poly(phenylene ether ether ketone) composition (A-1) obtained in Reference Example 1 with potassium 4-phenylphenoxide (B-1) as a polymerization initiator was placed in a glass ampoule bottle, the inside of the ampoule bottle was substituted with nitrogen. The mixing ratio of this polymerization initiator (B-1) was 5 mol % relative to the repeating unit expressed by a formula —(O-Ph-O-Ph-CO-Ph)-, which is the primary structural unit of the cyclic poly(phenylene ether ether ketone). The ampoule bottle was placed in an electric oven at the temperature controlled to 320° C., was heated for 30 minutes and was subsequently taken out of the electric oven to be cooled down to room temperature. A black solid matter was then obtained.

The result of analysis using a differential scanning calorimeter showed that the black solid matter had the melting point of 340° C. It was also shown that the black solid matter was fully dissolved in 98% by weight of concentrated sulfuric acid and had the reduced viscosity of 0.75 dL/g and the intrinsic viscosity of 0.72 dL/g.

Example 4

Production of Poly(Phenylene Ether Ether Ketone)

After 200 mg of a powder mixture of the cyclic poly(phenylene ether ether ketone) composition (A-1) obtained in Reference Example 1 with potassium 4-phenylphenoxide (B-1) as a polymerization initiator was placed in a glass ampoule bottle, the inside of the ampoule bottle was substituted with nitrogen. The mixing ratio of this polymerization initiator (B-1) was 5 mol % relative to the repeating unit expressed by a formula —(O-Ph-O-Ph-CO-Ph)-, which is the primary structural unit of the cyclic poly(phenylene ether ether ketone). The ampoule bottle was placed in an electric oven at the temperature controlled to 360° C., was heated for 180 minutes and was subsequently taken out of the electric oven to be cooled down to room temperature. A black solid matter was then obtained.

The result of analysis using a differential scanning calorimeter showed that the black solid matter had the melting point of 344° C. It was also shown that the black solid matter was fully dissolved in 98% by weight of concentrated sulfuric acid and had the reduced viscosity of 0.75 dL/g and the intrinsic viscosity of 0.72 dL/g.

Additionally, the obtained black solid matter was modified according to the technique described in Macromolecules, volume 42, page 1955 (2009) by the procedure described above. The procedure added 1.3 mL of dichloromethane, 0.3 mL of trifluoroacetic acid, 50 mg of 1,2-ethane dithiol and 37 mg of boron trifluoride diethyl ether complex to about 103 mg of the obtained black solid matter, stirred the solution mixture under nitrogen at room temperature for 18 hours, added the solution mixture dropwise to 10 mL of methanol and collected a precipitating white solid matter by using a Hirsch funnel. The result of GPC measurement of the obtained white solid matter showed that the polydispersity (Mw/Mn) was 5.3. The result of NMR measurement of the obtained white solid matter showed that a phenyl phenoxide group derived from potassium 4-phenylphenoxide was introduced into the terminal group.

Example 5

Production of Poly(Phenylene Ether Ether Ketone)

After 200 mg of a powder mixture of the cyclic poly(phenylene ether ether ketone) composition (A-1) obtained in Reference Example 1 with potassium 4-benzoylphenoxide (B-2) as a polymerization initiator was placed in a glass ampoule bottle, the inside of the ampoule bottle was substituted with nitrogen. The mixing ratio of this polymerization initiator (B-2) was 5 mol % relative to the repeating unit expressed by a formula —(O-Ph-O-Ph-CO-Ph)-, which is the primary structural unit of the cyclic poly(phenylene ether ether ketone). The ampoule bottle was placed in an electric oven at the temperature controlled to 300° C., was heated for 30 minutes and was subsequently taken out of the electric oven to be cooled down to room temperature. A black solid matter was then obtained.

The result of analysis using a differential scanning calorimeter showed that the black solid matter had the melting point of 340° C. It was also shown that the black solid matter was fully dissolved in 98% by weight of concentrated sulfuric acid and had the reduced viscosity of 0.70 dL/g and the intrinsic viscosity of 0.68 dL/g.

Example 6

Production of Poly(Phenylene Ether Ether Ketone)

After 200 mg of a powder mixture of the cyclic poly(phenylene ether ether ketone) composition (A-1) obtained in Reference Example 1 with potassium 4-benzlphenoxide (B-3) as a polymerization initiator was placed in a glass ampoule bottle, the inside of the ampoule bottle was substituted with nitrogen. The mixing ratio of this polymerization initiator (B-3) was 5 mol % relative to the repeating unit expressed by a formula —(O-Ph-O-Ph-CO-Ph)-, which is the primary structural unit of the cyclic poly(phenylene ether ether ketone). The ampoule bottle was placed in an electric oven at the temperature controlled to 300° C., was heated for 30 minutes and was subsequently taken out of the electric oven to be cooled down to room temperature. A black solid matter was then obtained.

The result of analysis using a differential scanning calorimeter showed that the black solid matter had the melting point of 336° C. It was also shown that the black solid matter was fully dissolved in 98% by weight of concentrated sulfuric acid and had the reduced viscosity of 0.72 dL/g and the intrinsic viscosity of 0.70 dL/g.

Example 7

Production of Poly(Phenylene Ether Ether Ketone)

After 200 mg of a powder mixture of the cyclic poly(phenylene ether ether ketone) composition (A-1) obtained in Reference Example 1 with potassium 4-phenylphenoxide (B-1) as a polymerization initiator and 4-fluorobenzophenone (C-1) as an additive was placed in a glass ampoule bottle, the inside of the ampoule bottle was substituted with nitrogen. The mixing ratio of this polymerization initiator (B-1) was 5 mol % relative to the repeating unit expressed by a formula —(O-Ph-O-Ph-CO-Ph)-, which is the primary structural unit of the cyclic poly(phenylene ether ether ketone). The mixing ratio of the additive (C-1) was 1 mol % relative to the repeating unit expressed by a formula —(O-Ph-O-Ph-CO-Ph)-, which is the primary structural unit of the cyclic poly(phenylene ether ether ketone). The ampoule bottle was placed in an electric oven at the temperature controlled to 360° C., was heated for 180 minutes and was subsequently taken out of the electric oven to be cooled down to room temperature. A black solid matter was then obtained.

The result of analysis using a differential scanning calorimeter showed that the black solid matter had the melting point of 340° C. It was also shown that the black solid matter was fully dissolved in 98% by weight of concentrated sulfuric acid and had the reduced viscosity of 0.72 dL/g and the intrinsic viscosity of 0.71 dL/g.

Additionally, the obtained black solid matter was modified according to the technique described in Macromolecules, volume 42, page 1955 (2009) by the procedure described above. The procedure added 1.3 mL of dichloromethane, 0.3 mL of trifluoroacetic acid, 47 mg of 1,2-ethane dithiol and 35 mg of boron trifluoride diethyl ether complex to 100 mg of the obtained black solid matter, stirred the solution mixture under nitrogen at room temperature for 18 hours, added the solution mixture dropwise to 10 mL of methanol and collected a precipitating white solid matter by using a Hirsch funnel. The result of GPC measurement of the obtained white solid matter showed that the polydispersity (Mw/Mn) was 3.7. The result of NMR measurement of the obtained white solid matter showed that a phenyl phenoxide group derived from potassium 4-phenylphenoxide and a benzophenone group derived from 4-fluorobenzophenone were introduced into the terminal group.

Example 8

Production of Poly(Phenylene Ether Ether Ketone)

After 202 mg of a powder mixture of the cyclic poly(phenylene ether ether ketone) composition (A-1) obtained in Reference Example 1 with potassium 4-phenylphenoxide (B-1) as a polymerization initiator and 4-fluorobenzophenone (C-1) as an additive was placed in a glass ampoule bottle, the inside of the ampoule bottle was substituted with nitrogen. The mixing ratio of this polymerization initiator (B-1) was 5 mol % relative to the repeating unit expressed by a formula —(O-Ph-O-Ph-CO-Ph)-, which is the primary structural unit of the cyclic poly(phenylene ether ether ketone). The mixing ratio of the additive (C-1) was 5 mol % relative to the repeating unit expressed by a formula —(O-Ph-O-Ph-CO-Ph)-, which is the primary structural unit of the cyclic poly(phenylene ether ether ketone). The ampoule bottle was placed in an electric oven at the temperature controlled to 360° C., was heated for 180 minutes and was subsequently taken out of the electric oven to be cooled down to room temperature. A black solid matter was then obtained.

The result of analysis using a differential scanning calorimeter showed that the black solid matter had the melting point of 340° C. It was also shown that the black solid matter was fully dissolved in 98% by weight of concentrated sulfuric acid and had the reduced viscosity of 0.70 dL/g and the intrinsic viscosity of 0.69 dL/g.

Additionally, the obtained black solid matter was modified according to the technique described in Macromolecules, volume 42, page 1955 (2009) by the procedure described above. The procedure added 1.3 mL of dichloromethane, 0.3 mL of trifluoroacetic acid, 48 mg of 1,2-ethane dithiol and 37 mg of boron trifluoride diethyl ether complex to 105 mg of the obtained black solid matter, stirred the solution mixture under nitrogen at room temperature for 18 hours, added the solution mixture dropwise to 10 mL of methanol and collected a precipitating white solid matter by using a Hirsch funnel. The result of GPC measurement of the obtained white solid matter showed that the polydispersity (Mw/Mn) was 3.3. The result of NMR measurement of the obtained white solid matter showed that a phenyl phenoxide group derived from potassium 4-phenylphenoxide and a benzophenone group derived from 4-fluorobenzophenone were introduced into the terminal group.

Example 9

Production of Poly(Phenylene Ether Ether Ketone)

After 200 mg of a powder mixture of the cyclic poly(phenylene ether ether ketone) composition (A-1) obtained in Reference Example 1 with potassium 4-phenylphenoxide (B-1) as a polymerization initiator was placed in a glass ampoule bottle, the inside of the ampoule bottle was substituted with nitrogen. The mixing ratio of this polymerization initiator (B-1) was 1 mol % relative to the repeating unit expressed by a formula —(O-Ph-O-Ph-CO-Ph)-, which is the primary structural unit of the cyclic poly(phenylene ether ether ketone). The ampoule bottle was placed in an electric oven at the temperature controlled to 320° C., was heated for 30 minutes and was subsequently taken out of the electric oven to be cooled down to room temperature. A black solid matter was then obtained.

The result of analysis using a differential scanning calorimeter showed that the black solid matter had the melting point of 338° C. It was also shown that the black solid matter was fully dissolved in 98% by weight of concentrated sulfuric acid and had the reduced viscosity of 1.40 dL/g and the intrinsic viscosity of 1.37 dL/g.

Example 10

Production of Poly(Phenylene Ether Ether Ketone)

After 200 mg of a powder mixture of the cyclic poly(phenylene ether ether ketone) composition (A-1) obtained in Reference Example 1 with potassium 4-phenylphenoxide (B-1) as a polymerization initiator was placed in a glass ampoule bottle, the inside of the ampoule bottle was substituted with nitrogen. The mixing ratio of this polymerization initiator (B-1) was 2 mol % relative to the repeating unit expressed by a formula —(O-Ph-O-Ph-CO-Ph)-, which is the primary structural unit of the cyclic poly(phenylene ether ether ketone). The ampoule bottle was placed in an electric oven at the temperature controlled to 320° C., was heated for 30 minutes and was subsequently taken out of the electric oven to be cooled down to room temperature. A black solid matter was then obtained.

The result of analysis using a differential scanning calorimeter showed that the black solid matter had the melting point of 340° C. It was also shown that the black solid matter was fully dissolved in 98% by weight of concentrated sulfuric acid and had the reduced viscosity of 1.07 dL/g and the intrinsic viscosity of 1.05 dL/g.

Example 11

Production of Poly(Phenylene Ether Ether Ketone)

After 200 mg of a powder mixture of the cyclic poly(phenylene ether ether ketone) composition (A-1) obtained in Reference Example 1 with potassium 4-phenylphenoxide (B-1) as a polymerization initiator was placed in a glass ampoule bottle, the inside of the ampoule bottle was substituted with nitrogen. The mixing ratio of this polymerization initiator (B-1) was 3 mol % relative to the repeating unit expressed by a formula —(O-Ph-O-Ph-CO-Ph)-, which is the primary structural unit of the cyclic poly(phenylene ether ether ketone). The ampoule bottle was placed in an electric oven at the temperature controlled to 320° C., was heated for 30 minutes and was subsequently taken out of the electric oven to be cooled down to room temperature. A black solid matter was then obtained.

The result of analysis using a differential scanning calorimeter showed that the black solid matter had the melting point of 345° C. It was also shown that the black solid matter was fully dissolved in 98% by weight of concentrated sulfuric acid and had the reduced viscosity of 0.92 dL/g and the intrinsic viscosity of 0.90 dL/g.

Comparative Example 1

Production of Poly(Phenylene Ether Ether Ketone)

After 200 mg of a powder mixture of the cyclic poly(phenylene ether ether ketone) composition (A-1) obtained in Reference Example 1 with cesium fluoride (B-4) as a polymerization initiator was placed in a glass ampoule bottle, the inside of the ampoule bottle was substituted with nitrogen. The mixing ratio of this polymerization initiator (B-4) was 5 mol % relative to the repeating unit expressed by a formula —(O-Ph-O-Ph-CO-Ph)-, which is the primary structural unit of the cyclic poly(phenylene ether ether ketone). The ampoule bottle was placed in an electric oven at the temperature controlled to 360° C., was heated for 180 minutes and was subsequently taken out of the electric oven to be cooled down to room temperature. A black solid matter was then obtained.

The result of analysis using a differential scanning calorimeter showed that the black solid matter had the melting point of 332° C. The black solid matter was partly insoluble in 98% by weight of concentrated sulfuric acid.

Comparative Example 2

Production of Poly(Phenylene Ether Ether Ketone)

After 200 mg of a powder mixture of the cyclic poly(phenylene ether ether ketone) composition (A-2) obtained in Reference Example 2 with potassium 4-phenylphenoxide (B-1) as a polymerization initiator was placed in a glass ampoule bottle, the inside of the ampoule bottle was substituted with nitrogen. The mixing ratio of this polymerization initiator (B-1) was 5 mol % relative to the repeating unit expressed by a formula —(O-Ph-O-Ph-CO-Ph)-, which is the primary structural unit of the cyclic poly(phenylene ether ether ketone). The ampoule bottle was placed in an electric oven at the temperature controlled to 300° C., was heated for 30 minutes and was subsequently taken out of the electric oven to be cooled down to room temperature. A black solid matter was then obtained.

The result of analysis using a differential scanning calorimeter showed that the black solid matter had the melting point of 308° C., which indicated insufficient progress of polymerization. It was also shown that the black solid matter was fully dissolved in 98% by weight of concentrated sulfuric acid and had the reduced viscosity and the intrinsic viscosity of not greater than 0.02 dL/g.

With regard to the respective Examples 1 to 11 and Comparative Examples 1 and 2, the conditions of the polymerization reactions and the physical properties examined for the resulting poly(phenylene ether ether ketone)s are collectively shown in Table 1 below.

when the polymerization reaction is performed at the lower heating temperature. This indicates the progress of polymerization. Moreover, comparison between Example 4 and Comparative Example 1 shows that using a metal phenoxide as a polymerization initiator obtains a homogeneous polymer substantially free from any undesired foreign matter in sulfuric acid. Additionally, comparison between Example 4 and Examples 7 and 8 shows that using an additive having an electron-withdrawing leaving group can readily control the polydispersity of the product obtained by the polymerization reaction in a narrower range.

The invention claimed is:

1. A production method of poly(phenylene ether ether ketone), the production method making a cyclic poly(phenylene ether ether ketone) composition subjected to thermal ring-opening polymerization in the presence of a metal phenoxide, wherein the cyclic poly(phenylene ether ether ketone) composition includes 60% by weight or more of cyclic poly(phenylene ether ether ketone) expressed by General Formula (I), the cyclic poly(phenylene ether ether ketone) is a cyclic poly(phenylene ether ether ketone) mixture having different integers m, and

TABLE 1

| | Material Composition | Initiator | Addition Amount of Initiator | Additive | Addition Amount of Additive | Heating Temp | Heating Time | Insoluble Part in Sulfuric Acid | Intrinsic Viscosity of Polymer | Polydispersity of Product |
|---|---|---|---|---|---|---|---|---|---|---|
| EX 1 | A-1 | B-1 | 5 mol % | — | — | 280° C. | 30 min | None | 0.60 dL/g | — |
| EX 2 | A-1 | B-1 | 5 mol % | — | — | 300° C. | 30 min | None | 0.69 dL/g | — |
| EX 3 | A-1 | B-1 | 5 mol % | — | — | 320° C. | 30 min | None | 0.72 dL/g | — |
| EX 4 | A-1 | B-1 | 5 mol % | — | — | 360° C. | 180 min | None | 0.72 dL/g | 5.3 |
| EX 5 | A-1 | B-2 | 5 mol % | — | — | 300° C. | 30 min | None | 0.68 dL/g | — |
| EX 6 | A-1 | B-3 | 5 mol % | — | — | 300° C. | 30 min | None | 0.70 dL/g | — |
| EX 7 | A-1 | B-1 | 5 mol % | C-1 | 1 mol % | 360° C. | 180 min | None | 0.71 dL/g | 3.7 |
| EX 8 | A-1 | B-1 | 5 mol % | C-1 | 5 mol % | 360° C. | 180 min | None | 0.69 dL/g | 3.3 |
| EX 9 | A-1 | B-1 | 1 mol % | — | — | 320° C. | 30 min | None | 1.37 dL/g | — |
| EX 10 | A-1 | B-1 | 2 mol % | — | — | 320° C. | 30 min | None | 1.05 dL/g | — |
| EX 11 | A-1 | B-1 | 3 mol % | — | — | 320° C. | 30 min | None | 0.90 dL/g | — |
| COMP EX 1 | A-1 | B-4 | 5 mol % | — | — | 360° C. | 180 min | Present | Unmeasurable | — |
| COMP EX 2 | A-2 | B-1 | 5 mol % | — | — | 300° C. | 30 min | None | 0.02 dL/g or lower | — |

"—" indicates "not contained" or "not measured".
(A-1) content of cyclic PEEK mixture = 85% by weight, consecutive integers m = 2 to 8, melting point= 159° C.
(A-2) content of cyclic PEEK mixture = 94% by weight, integers m = 3 and 6, melting point = 275° C.
(B-1) potassium 4-phenylphenoxide
(B-2) potassium 4-benzoylphenoxide
(B-3) potassium 4-benzylphenoxide
(B-4) cesium fluoride
(C-1) 4-fluorobenzophenone
PEEK: poly(phenylene ether ether ketone)

Examples and Comparative Examples of Table 1 clearly show the following. Comparison between Examples 1 to 3 and Comparative Example 2 shows that using only two different cyclic poly(phenylene ether ether ketone)s having the repeating numbers m=3 and 6 causes no substantial increase in viscosity of the composition obtained after the polymerization reaction. This indicates little progress of polymerization. Using seven different cyclic poly(phenylene ether ether ketone)s having the consecutive repeating numbers m=2 to 8, on the other hand, causes an increase in viscosity of the composition obtained after the polymerization reaction even the composition has a melting point of 270° C. or lower:

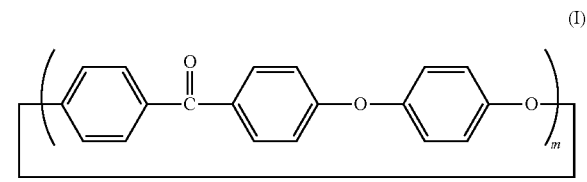

(I)

wherein m in Formula (I) represents an integer of 2 to 40, wherein the metal phenoxide is at least one selected among General Formulae below:

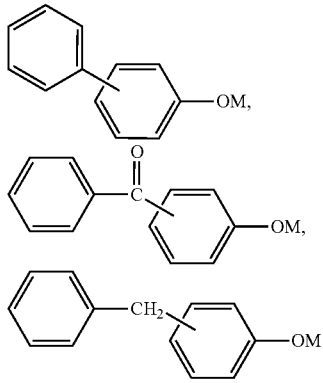

(wherein M represents at least one species selected among Li, Na, K and Cs).

2. The production method of poly(phenylene ether ether ketone) according to claim 1, wherein the thermal ring-opening polymerization is performed at a temperature of 335° C. or lower.

3. The production method of poly(phenylene ether ether ketone) according to claim 1, the production method adding the metal phenoxide to the cyclic poly(phenylene ether ether ketone) composition, such that an addition amount of the metal alkoxide and/or the metal phenoxide is 0.001 to 50 mol % relative to 1 mol of a repeating unit expressed by a formula —(O-Ph-O-Ph-CO-Ph)-, which is a primary structural unit of the cyclic poly(phenylene ether ether ketone).

4. The production method of poly(phenylene ether ether ketone) according to claim 1, wherein the cyclic poly(phenylene ether ether ketone) composition has a melting point of 250° C. or lower.

5. The production method of poly(phenylene ether ether ketone) according to claim 1, wherein the cyclic poly(phenylene ether ether ketone) composition has a melting point of 230° C. or lower.

6. The production method of poly(phenylene ether ether ketone) according to claim 1, the production method adding an additive which has an electron-withdrawing leaving group X and is expressed by a formula $R^2$—X to the cyclic poly(phenylene ether ether ketone) composition, such that an addition amount of the additive is 0.001 to 50 mol % relative to 1 mol of a repeating unit expressed by a formula —(O-Ph-O-Ph-CO-Ph)-, which is a primary structural unit of the cyclic poly(phenylene ether ether ketone), wherein $R^2$ represents an aliphatic group containing 1 to 20 carbon atoms or an aromatic group containing 6 to 30 carbon atoms, wherein an aromatic ring optionally includes an alkyl group, a phenyl group or another heteroatom-containing substituent group.

\* \* \* \* \*